(12) United States Patent
Mori et al.

(10) Patent No.: US 12,163,894 B2
(45) Date of Patent: Dec. 10, 2024

(54) SENSING SYSTEM AND STORAGE MEDIUM STORING DATA STRUCTURE USED IN SENSING SYSTEM

(71) Applicant: DENSO CORPORATION, Kariya (JP)

(72) Inventors: Hodaka Mori, Kariya (JP); Kazuki Koda, Kariya (JP); Kazuaki Mawatari, Kariya (JP)

(73) Assignee: DENSO CORPORATION, Kariya (JP)

( * ) Notice: Subject to any disclaimer, the term of this patent is extended or adjusted under 35 U.S.C. 154(b) by 725 days.

(21) Appl. No.: 17/394,289

(22) Filed: Aug. 4, 2021

(65) Prior Publication Data

US 2021/0364443 A1 Nov. 25, 2021

Related U.S. Application Data

(63) Continuation of application No. PCT/JP2020/003441, filed on Jan. 30, 2020.

(30) Foreign Application Priority Data

Feb. 8, 2019 (JP) .................................. 2019-021776

(51) Int. Cl.
*G01N 21/65* (2006.01)
*G01N 33/02* (2006.01)
(Continued)

(52) U.S. Cl.
CPC ......... *G01N 21/658* (2013.01); *G01N 33/025* (2013.01); *G06Q 10/04* (2013.01);
(Continued)

(58) Field of Classification Search
None
See application file for complete search history.

(56) References Cited

U.S. PATENT DOCUMENTS 9,728,388 B2 * 8/2017 Naya ................. H01J 49/0004
11,976,972 B2 * 5/2024 Rodriguez-Saona ......................
G01J 3/0264
(Continued)

FOREIGN PATENT DOCUMENTS

| JP | 2015-190836 A | 11/2015 |
|---|---|---|
| JP | 2016-202157 A | 12/2016 |
| JP | 2018-088198 A | 6/2018 |

*Primary Examiner* — Roy Y Yi
(74) *Attorney, Agent, or Firm* — Posz Law Group, PLC

(57) ABSTRACT

A server including a storage and a controller is communicably connected with a communication terminal. The storage is configured to store a processing data and an analysis data for each of a plurality of analysis targets. The processing data relates to a processing condition for forming a concavo-convex structure on a detection substrate to be used in performing a spectroscopic analysis. The analysis data is used to analyze the analysis target from a spectroscopic spectrum of the analysis target obtained by the spectroscopy analysis. Upon receiving a signal requesting the processing data, the controller is configured to select the processing data corresponding to the analysis target and transmit the selected processing data to the communication terminal. Upon receiving a spectroscopic spectrum, the controller is configured to use the analysis data to analyze the spectroscopic spectrum.

17 Claims, 22 Drawing Sheets

(51) Int. Cl.
*G06Q 10/04* (2023.01)
*G06Q 50/02* (2024.01)
*G16Y 10/05* (2020.01)
*G16Y 40/20* (2020.01)

(52) U.S. Cl.
CPC .............. *G06Q 50/02* (2013.01); *G16Y 10/05* (2020.01); *G16Y 40/20* (2020.01); *G01N 2201/06113* (2013.01)

(56) References Cited

U.S. PATENT DOCUMENTS

| | | |
|---|---|---|
| 2010/0324203 A1 | 12/2010 | Moutinho et al. |
| 2011/0181878 A1* | 7/2011 | Parng .................. G01N 21/658 356/301 |
| 2012/0129975 A1 | 5/2012 | Moutinho et al. |

\* cited by examiner

FIG. 8A i: DATE/TIME, ii: TEMPERATURE OUTSIDE HOUSE, iii: HUMIDITY OUTSIDE HOUSE, iv: AIR VOLUME, v: SOLAR RADIATION AMOUNT, vi: TEMPERATURE INSIDE HOUSE, vii: HUMIDITY INSIDE HOUSE, viii: CULTURE SOLUTION CONCENTRATION, ix: CULTURE SOLUTION AMOUNT, x: NUMBER OF LEAVES THINNED OUT, xi: NUMBER OF LEAVES, xii: AVERAGE STEM THICKNESS, xiii: STEM HEIGHT GROWING PERIOD: X(t) AND Y(t)
HARVESTING PERIOD: X(t)
GROWING PERIOD: X(t)
CONDITION DATA

| VARIABLE / GROWING STATUS | i | ii | iii | iv | v | vi | vii | viii | ix | x | xi | xii | xiii |
|---|---|---|---|---|---|---|---|---|---|---|---|---|---|
| GROWING PERIOD | 2018/10/22 | 23.95 | 60.47 | 0.13 | 1.00 | 20 | 60 | 1.07 | 103.22 | 0 | 1 | 1 | 2 |
| GROWING PERIOD | 2018/10/23 | 21.78 | 63.52 | 0.10 | 1.04 | 20 | 60 | 1.04 | 107.54 | 0 | 1 | 1 | 3 |
| GROWING PERIOD | 2018/10/24 | 22.31 | 61.51 | 0.25 | 1.07 | 20 | 60 | 1.09 | 101.30 | 0 | 1 | 1 | 3 |
| GROWING PERIOD | 2018/10/25 | 22.02 | 69.63 | 0.07 | 1.05 | 20 | 65 | 1.07 | 103.33 | 0 | 2 | 1 | 3 |
| GROWING PERIOD | 2018/10/26 | 20.11 | 64.15 | 0.04 | 1.04 | 20 | 66 | 1.04 | 109.77 | 0 | 4 | 1 | 3 |
| GROWING PERIOD | 2018/10/27 | 20.83 | 62.04 | 0.27 | 1.08 | 25 | 60 | 1.04 | 102.56 | 1 | 8 | 2 | 4 |
| GROWING PERIOD | 2018/10/28 | 22.82 | 66.06 | 0.06 | 1.07 | 25 | 60 | 1.03 | 104.14 | 3 | 10 | 2 | 4 |
| GROWING PERIOD | 2018/10/29 | 24.30 | 62.06 | 0.15 | 1.08 | 25 | 80 | 1.10 | 104.13 | 0 | 20 | 2 | 4 |

FIG. 9A i: DATE/TIME, ii: TEMPERATURE OUTSIDE HOUSE, iii: HUMIDITY OUTSIDE HOUSE, iv: AIR VOLUME, v: SOLAR RADIATION AMOUNT, vi: TEMPERATURE INSIDE HOUSE, vii: HUMIDITY INSIDE HOUSE, viii: CULTURE SOLUTION CONCENTRATION, ix: CULTURE SOLUTION AMOUNT, x: NUMBER OF LEAVES THINNED OUT, xi: NUMBER OF LEAVES, xii: AVERAGE STEM THICKNESS, xiii: STEM HEIGHT

| Variable / Growing Status | i | ii | iii | iv | v | vi | vii | viii | ix | x | xi | xii | xiii |
|---|---|---|---|---|---|---|---|---|---|---|---|---|---|
| GROWING PERIOD | 2018/10/22 | 23.95 | 60.47 | 0.13 | 1.00 | 20 | 60 | 1.07 | 103.22 | 0 | 1 | 1 | 2 |
| GROWING PERIOD | 2018/10/23 | 21.78 | 63.52 | 0.10 | 1.04 | 20 | 60 | 1.04 | 107.54 | 0 | 1 | 1 | 3 |
| GROWING PERIOD | 2018/10/24 | 22.31 | 61.51 | 0.25 | 1.07 | 20 | 60 | 1.09 | 101.30 | 0 | 1 | 1 | 3 |
| GROWING PERIOD | 2018/10/25 | 22.02 | 69.63 | 0.07 | 1.05 | 20 | 65 | 1.07 | 103.33 | 0 | 2 | 1 | 3 |
| GROWING PERIOD | 2018/10/26 | 20.11 | 64.15 | 0.04 | 1.04 | 20 | 66 | 1.04 | 109.77 | 0 | 4 | 1 | 3 |
| GROWING PERIOD | 2018/10/27 | 20.83 | 62.04 | 0.27 | 1.08 | 25 | 60 | 1.04 | 102.56 | 1 | 8 | 2 | 3 |
| GROWING PERIOD | 2018/10/28 | 22.82 | 66.06 | 0.06 | 1.07 | 25 | 60 | 1.03 | 104.14 | 3 | 10 | 2 | 4 |
| GROWING PERIOD | 2018/10/29 | 24.30 | 62.06 | 0.15 | 1.08 | 25 | 80 | 1.10 | 104.13 | 0 | 20 | 2 | 4 |
| GROWING PERIOD | 2018/10/30 | 20.10 | 68.76 | 0.46 | 1.08 | 22 | 80 | 1.03 | 106.08 | 2 | 21 | 3 | 4 |
| GROWING PERIOD | 2018/10/31 | 20.63 | 62.85 | 0.35 | 1.07 | 25 | 70 | 1.09 | 104.60 | 3 | 22 | 3 | 5 |
| GROWING PERIOD | 2018/11/1 | 23.12 | 61.61 | 0.22 | 1.00 | 26 | 50 | 1.07 | 106.16 | 5 | 23 | 3 | 6 |
| GROWING PERIOD | 2018/11/2 | 22.51 | 64.24 | 0.46 | 1.06 | 20 | 50 | 1.01 | 105.43 | 4 | 24 | 4 | 6 |
| GROWING PERIOD | 2018/11/3 | 24.74 | 62.04 | 0.25 | 1.05 | 20 | 20 | 1.07 | 108.33 | 3 | 25 | 4 | 6 |

GROWING PERIOD: X(t)
HARVESTING PERIOD: X(t)
CONDITION DATA
GROWING PERIOD: X(t) AND Y(t)

xiv: LEAF SERS SPECTRUM SHAPE, xv: LEAF SERS SPECTRUM PEAK HEIGHT OF SUBSTANCE α, xvi: CONCENTRATION OF SUBSTANCE α,
xvii: FRUIT SERS SPECTRUM SHAPE, xviii: FRUIT SERS SPECTRUM PEAK HEIGHT OF SUBSTANCE β, xix: CONCENTRATION OF SUBSTANCE β

| Variable / Growing status | xiv | xv | xvi | xvii | xviii | xix |
|---|---|---|---|---|---|---|
| GROWING PERIOD | a | 5.41 | 57.12 | | | |
| | b | 6.10 | 63.87 | | | |
| | c | 3.00 | 30.13 | | | |
| | d | 1.34 | 13.75 | | | |
| | e | 7.10 | 71.00 | | | |
| | f | 2.62 | 27.59 | | | |
| | g | 4.82 | 48.17 | | | |
| | h | 5.98 | 63.22 | | | |
| | i | 6.17 | 64.90 | | | |
| | j | 3.44 | 37.74 | | | |
| | k | 9.08 | 93.11 | | | |
| | l | 4.43 | 45.29 | | | |
| | m | 8.71 | 92.97 | | | |
| HARVESTING PERIOD | | | | | | |

FIG. 9C xx: NUMBER OF HARVESTABLE FRUITS, xxi: AVERAGE SIZE OF HARVESTABLE FRUITS, xxii: SIZE DISPERSION, xxiii: NUMBER OF HARVESTS $Y(t)$ STATUS DATA

| VARIABLE / GROWING STATUS | xx | xxi | xxii | xxiii |
|---|---|---|---|---|
| GROWING PERIOD | ○○○○○○○○○○○○ | ○○○○○○○○○○○○ | ○○○○○○○○○○○○ | ○○○○○○○○○○○○ |
| HARVESTING PERIOD | | | | |

FIG. 10A i: DATE/TIME, ii: TEMPERATURE INSIDE HOUSE, iii: TEMPERATURE OUTSIDE HOUSE, iv: AIR VOLUME, v: SOLAR RADIATION AMOUNT, vi: TEMPERATURE INSIDE HOUSE, vii: HUMIDITY INSIDE HOUSE, viii: CULTURE SOLUTION CONCENTRATION, ix: CULTURE SOLUTION AMOUNT, x: NUMBER OF LEAVES THINNED OUT, xi: NUMBER OF LEAVES, xii: AVERAGE STEM THICKNESS, xiii: STEM HEIGHT

| Variable / Growing Status | i | ii | iii | iv | v | vi | vii | viii | ix | x | xi | xii | xiii |
|---|---|---|---|---|---|---|---|---|---|---|---|---|---|
| GROWING PERIOD | 2018/10/22 | 23.95 | 60.47 | 0.13 | 1.00 | 20 | 60 | 1.07 | 103.22 | 0 | 1 | 1 | 2 |
| GROWING PERIOD | 2018/10/23 | 21.78 | 63.52 | 0.10 | 1.04 | 20 | 60 | 1.04 | 107.54 | 0 | 1 | 1 | 3 |
| GROWING PERIOD | 2018/10/24 | 22.31 | 61.51 | 0.25 | 1.07 | 20 | 60 | 1.09 | 101.30 | 0 | 1 | 1 | 3 |
| GROWING PERIOD | 2018/10/25 | 22.02 | 69.63 | 0.07 | 1.05 | 20 | 65 | 1.07 | 103.33 | 0 | 2 | 1 | 3 |
| GROWING PERIOD | 2018/10/26 | 20.11 | 64.15 | 0.04 | 1.04 | 20 | 66 | 1.04 | 109.77 | 1 | 4 | 1 | 3 |
| GROWING PERIOD | 2018/10/27 | 20.83 | 62.04 | 0.27 | 1.08 | 25 | 60 | 1.04 | 102.56 | 3 | 8 | 2 | 3 |
| GROWING PERIOD | 2018/10/28 | 22.82 | 66.06 | 0.06 | 1.07 | 25 | 60 | 1.03 | 104.14 | 0 | 10 | 2 | 4 |
| GROWING PERIOD | 2018/10/29 | 24.30 | 62.06 | 0.15 | 1.08 | 25 | 80 | 1.10 | 104.13 | 2 | 20 | 2 | 4 |
| GROWING PERIOD | 2018/10/30 | 20.10 | 68.76 | 0.46 | 1.08 | 22 | 80 | 1.03 | 106.08 | 5 | 21 | 3 | 4 |
| GROWING PERIOD | 2018/10/31 | 20.63 | 62.85 | 0.35 | 1.07 | 25 | 70 | 1.09 | 104.60 | 4 | 22 | 4 | 4 |
| GROWING PERIOD | 2018/11/1 | 23.12 | 61.61 | 0.22 | 1.00 | 26 | 50 | 1.07 | 106.16 | 3 | 23 | 4 | 5 |
| GROWING PERIOD | 2018/11/2 | 22.51 | 64.24 | 0.46 | 1.06 | 20 | 50 | 1.01 | 105.43 | 5 | 24 | 4 | 6 |
| GROWING PERIOD | 2018/11/3 | 24.74 | 62.04 | 0.25 | 1.05 | 25 | 20 | 1.07 | 108.33 | 3 | 25 | 4 | 6 |
| GROWING PERIOD | 2018/11/4 | 20.97 | 68.17 | 0.25 | 1.00 | 25 | 80 | 1.02 | 102.32 | 5 | 26 | 4 | 7 |
| GROWING PERIOD | 2018/11/5 | 21.00 | 69.48 | 0.38 | 1.09 | 25 | 80 | 1.10 | 107.30 | 3 | 27 | 4 | 7 |
| GROWING PERIOD | 2018/11/6 | 21.68 | 65.04 | 0.36 | 1.02 | 25 | 80 | 1.03 | 104.31 | 7 | 28 | 5 | 7 |
| HARVESTING PERIOD | 2018/11/7 | 20.31 | 63.05 | 0.38 | 1.08 | 22 | 60 | 1.03 | 107.98 | 8 | 28 | 5 | 7 |
| HARVESTING PERIOD | 2018/11/8 | 21.70 | 63.35 | 0.35 | 1.08 | 25 | 50 | 1.07 | 100.43 | 2 | 30 | 5 | 7 |
| HARVESTING PERIOD | 2018/11/9 | 24.16 | 64.95 | 0.43 | 1.06 | 26 | 40 | 1.06 | 103.75 | 4 | 32 | 5 | 8 |
| HARVESTING PERIOD | 2018/11/10 | 24.75 | 64.47 | 0.38 | 1.01 | 25 | 50 | 1.07 | 100.50 | 3 | 32 | 5 | 8 |
| HARVESTING PERIOD | 2018/11/11 | 23.79 | 67.24 | 0.27 | 1.02 | 26 | 50 | 1.01 | 106.78 | 5 | 31 | 5 | 8 |
| HARVESTING PERIOD | 2018/11/12 | 20.88 | 64.75 | 0.32 | 1.07 | 25 | 50 | 1.09 | 103.06 | 3 | 30 | 5 | 8 |
| HARVESTING PERIOD | 2018/11/13 | 20.29 | 66.78 | 0.05 | 1.01 | 20 | 65 | 1.10 | 102.86 | 7 | 32 | 5 | 8 |
| HARVESTING PERIOD | 2018/11/14 | 21.00 | 69.45 | 0.05 | 1.01 | 20 | 66 | 1.03 | 109.66 | 6 | 32 | 5 | 8 |
| HARVESTING PERIOD | 2018/11/15 | 21.92 | 67.87 | 0.05 | 1.03 | 25 | 60 | 1.08 | 101.16 | 9 | 30 | 5 | 8 |
| HARVESTING PERIOD | 2018/11/16 | 24.02 | 61.17 | 0.00 | 1.04 | 25 | 60 | 1.04 | 109.94 | 4 | 32 | 5 | 8 |
| HARVESTING PERIOD | 2018/11/17 | 24.50 | 69.32 | 0.25 | 1.03 | 25 | 80 | 1.05 | 104.60 | 3 | 31 | 5 | 8 |

GROWING PERIOD: X(t)  
HARVESTING PERIOD: X(t) CONDITION DATA  
GROWING PERIOD: X(t) AND Y(t)

xiv: LEAF SERS SPECTRUM SHAPE, xv: LEAF SERS SPECTRUM PEAK HEIGHT OF SUBSTANCE α, xvi: CONCENTRATION OF SUBSTANCE β,
xvii: FRUIT SERS SPECTRUM SHAPE, xviii: FRUIT SERS SPECTRUM PEAK HEIGHT OF SUBSTANCE β, xix: CONCENTRATION OF SUBSTANCE β

FIG. 10C xx : NUMBER OF HARVESTABLE FRUITS, xxi : AVERAGE SIZE OF HARVESTABLE FRUITS, xxii : SIZE DISPERSION, xxiii : NUMBER OF HARVESTS

| Growing Status \ Variable | Status Data Y(t) | | | |
|---|---|---|---|---|
| | xx | xxi | xxii | xxiii |
| GROWING PERIOD | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| HARVESTING PERIOD | 1 | 5 | 0 | 1 |
| | 2 | 7 | 1 | 2 |
| | 3 | 8 | 2 | 3 |
| | 5 | 8 | 3 | 5 |
| | 10 | 10.2 | 1.5 | 10 |
| | 20 | 11.7 | 1.6 | 20 |
| | 25 | 10.3 | 2.0 | 25 |
| | 30 | 11.0 | 1.0 | 30 |

FIG. 11A i: DATE/TIME, ii: TEMPERATURE OUTSIDE HOUSE, iii: HUMIDITY OUTSIDE HOUSE, iv: AIR VOLUME, v: SOLAR RADIATION AMOUNT, vi: TEMPERATURE INSIDE HOUSE, vii: HUMIDITY INSIDE HOUSE, viii: CULTURE SOLUTION CONCENTRATION, ix: CULTURE SOLUTION AMOUNT, x: NUMBER OF LEAVES THINNED OUT, xi: NUMBER OF LEAVES, xii: AVERAGE STEM THICKNESS, xiii: STEM HEIGHT

| VARIABLE / GROWING STATUS | i | ii | iii | iv | v | vi | vii | viii | ix | x | xi | xii | xiii |
|---|---|---|---|---|---|---|---|---|---|---|---|---|---|
| | | | | | GROWING PERIOD: X(t) | | | CONDITION DATA | | | | GROWING PERIOD: X(t) AND Y(t) | |
| | | | | | | | | HARVESTING PERIOD: X(t) | | | | | |
| GROWING PERIOD | 2018/10/22 | 23.95 | 60.47 | 0.13 | 1.00 | 20 | 60 | 1.07 | 103.22 | 0 | 1 | 1 | 2 |
| | 2018/10/23 | 21.78 | 63.52 | 0.10 | 1.04 | 20 | 60 | 1.04 | 107.54 | 0 | 1 | 1 | 3 |
| | 2018/10/24 | 22.31 | 61.51 | 0.25 | 1.07 | 20 | 60 | 1.09 | 101.30 | 0 | 1 | 1 | 3 |
| | 2018/10/25 | 22.02 | 69.63 | 0.07 | 1.05 | 20 | 65 | 1.07 | 103.33 | 0 | 2 | 1 | 3 |
| | 2018/10/26 | 20.11 | 64.15 | 0.04 | 1.04 | 20 | 66 | 1.04 | 109.77 | 0 | 4 | 1 | 3 |
| | 2018/10/27 | 20.83 | 62.04 | 0.27 | 1.08 | 25 | 60 | 1.04 | 102.56 | 1 | 8 | 2 | 3 |
| | 2018/10/28 | 22.82 | 66.06 | 0.06 | 1.07 | 25 | 60 | 1.03 | 104.14 | 3 | 10 | 2 | 4 |
| | 2018/10/29 | 24.30 | 62.06 | 0.15 | 1.08 | 25 | 80 | 1.10 | 104.13 | 0 | 20 | 2 | 4 |
| | 2018/10/30 | 20.10 | 68.76 | 0.46 | 1.08 | 22 | 80 | 1.03 | 106.08 | 2 | 21 | 3 | 4 |
| | 2018/10/31 | 20.63 | 62.85 | 0.35 | 1.07 | 25 | 70 | 1.09 | 104.60 | 3 | 22 | 3 | 5 |
| | 2018/11/1 | 23.12 | 61.61 | 0.22 | 1.00 | 26 | 50 | 1.07 | 106.16 | 5 | 23 | 4 | 6 |
| | 2018/11/2 | 22.51 | 64.24 | 0.46 | 1.06 | 20 | 50 | 1.01 | 105.43 | 4 | 24 | 4 | 6 |
| | 2018/11/3 | 24.74 | 62.04 | 0.25 | 1.05 | 25 | 20 | 1.07 | 108.33 | 3 | 25 | 4 | 7 |
| | 2018/11/4 | 20.97 | 68.17 | 0.25 | 1.00 | 25 | 80 | 1.02 | 102.32 | 5 | 26 | 4 | 7 |
| | 2018/11/5 | 21.00 | 69.48 | 0.38 | 1.09 | 25 | 80 | 1.10 | 107.30 | 3 | 27 | 4 | 7 |
| | 2018/11/6 | 21.68 | 65.04 | 0.36 | 1.02 | 25 | 80 | 1.03 | 104.31 | 7 | 28 | 5 | 7 |
| | 2018/11/7 | 20.31 | 63.05 | 0.38 | 1.08 | 22 | 80 | 1.03 | 107.98 | 8 | 28 | 5 | 7 |
| | 2018/11/8 | 21.70 | 63.35 | 0.35 | 1.08 | 25 | 60 | 1.06 | 100.43 | 2 | 30 | 5 | 8 |
| | 2018/11/9 | 24.16 | 64.95 | 0.43 | 1.06 | 26 | 50 | 1.07 | 103.75 | 4 | 32 | 5 | 8 |
| HARVESTING PERIOD | 2018/11/10 | 24.75 | 64.47 | 0.38 | 1.01 | 25 | 40 | 1.07 | 100.50 | 3 | 32 | 5 | 8 |
| | 2018/11/11 | 23.79 | 23.79 | 0.27 | 1.02 | 26 | 50 | 1.01 | 106.78 | 5 | 31 | 5 | 8 |
| | 2018/11/12 | 20.88 | 64.75 | 0.32 | 1.07 | 25 | 50 | 1.09 | 103.06 | 3 | 30 | 5 | 8 |
| | 2018/11/13 | 20.29 | 66.78 | 0.05 | 1.01 | 20 | 65 | 1.10 | 102.86 | 7 | 32 | 5 | 8 |
| | 2018/11/14 | 21.00 | 69.45 | 0.05 | 1.01 | 25 | 66 | 1.03 | 109.66 | 6 | 32 | 5 | 8 |
| | 2018/11/15 | 21.92 | 67.87 | 0.05 | 1.05 | 25 | 60 | 1.08 | 101.16 | 9 | 30 | 5 | 8 |
| | 2018/11/16 | 24.02 | 61.17 | 0.00 | 1.10 | 25 | 60 | 1.04 | 109.94 | 4 | 32 | 5 | 8 |
| | 2018/11/17 | 24.50 | 69.32 | 0.25 | 1.05 | 25 | 80 | 1.05 | 104.60 | 3 | 31 | 5 | 8 |
| | 2018/11/18 | 24.16 | 63.52 | 0.29 | 1.05 | 25 | 80 | 1.03 | 107.75 | 3 | 30 | 5 | 8 |
| | 2018/11/19 | 20.72 | 63.83 | 0.11 | 1.10 | 25 | 70 | 1.08 | 104.66 | 1 | 33 | 5 | 8 |
| | 2018/11/20 | 23.07 | 67.05 | 0.40 | 1.05 | 22 | 50 | 1.10 | 105.58 | 8 | 32 | 5 | 8 |
| | 2018/11/21 | 20.85 | 68.75 | 0.29 | 1.07 | 25 | 50 | 1.01 | 101.10 | 3 | 30 | 5 | 8 |
| | 2018/11/22 | 23.55 | 64.97 | 0.47 | 1.02 | 26 | 20 | 1.00 | 103.07 | 0 | 31 | 5 | 8 |
| | 2018/11/23 | 24.70 | 65.93 | 0.11 | 1.08 | 20 | 80 | 1.04 | 100.90 | 2 | 30 | 5 | 8 |
| | 2018/11/24 | 23.17 | 60.10 | 0.41 | 1.02 | 25 | 80 | 1.06 | 102.17 | 0 | 32 | 5 | 8 |
| | 2018/11/25 | 20.31 | 61.79 | 0.09 | 1.02 | 25 | 60 | 1.08 | 105.07 | 5 | 31 | 5 | 8 |
| | 2018/11/26 | 20.92 | 64.96 | 0.08 | 1.02 | 25 | 60 | 1.08 | 105.51 | | | 5 | 8 |
| | 2018/11/27 | 21.84 | 64.01 | 0.36 | 1.06 | 25 | 60 | 1.08 | 102.64 | 4 | 30 | 5 | 8 |
| | 2018/11/28 | 23.98 | 66.02 | 0.19 | 1.08 | 25 | 50 | 1.06 | 100.90 | 1 | 33 | 5 | 8 |

FIG. 11B xiv: LEAF SERS SPECTRUM SHAPE, xv: LEAF SERS SPECTRUM PEAK HEIGHT OF SUBSTANCE $\alpha$, xvi: CONCENTRATION OF SUBSTANCE $\alpha$, 
xvii: FRUIT SERS SPECTRUM SHAPE, xviii: FRUIT SERS SPECTRUM PEAK HEIGHT OF SUBSTANCE $\beta$, xix: CONCENTRATION OF SUBSTANCE $\beta$

| Growing Status \ Variable | xiv | xv | xvi | xvii | xviii | xix |
|---|---|---|---|---|---|---|
| GROWING PERIOD | a | 5.41 | 57.12 | | | |
| | b | 6.10 | 63.87 | | | |
| | c | 3.00 | 30.13 | | | |
| | d | 1.34 | 13.75 | | | |
| | e | 7.10 | 71.00 | | | |
| | f | 2.62 | 27.59 | | | |
| | g | 4.82 | 48.17 | | | |
| | h | 5.98 | 63.22 | | | |
| | i | 6.17 | 64.90 | | | |
| | j | 3.44 | 37.74 | | | |
| | k | 9.08 | 93.11 | | | |
| | l | 4.43 | 45.29 | | | |
| | m | 8.71 | 92.97 | | | |
| | n | 6.57 | 65.95 | | | |
| | o | 2.81 | 30.56 | | | |
| | p | 9.67 | 100.84 | | | |
| | q | 0.78 | 8.40 | | | |
| | r | 9.10 | 96.80 | | | |
| | s | 7.38 | 78.46 | | | |
| | t | 6.45 | 68.65 | | | |
| | u | 7.69 | 79.72 | | | |
| | v | 8.78 | 90.69 | | | |
| | w | 8.86 | 93.38 | | | |
| | x | 3.59 | 38.11 | | | |
| | y | 4.29 | 45.05 | | | |
| | z | 5.53 | 59.22 | | | |
| | aa | 1.25 | 13.02 | | | |
| | ab | 7.35 | 75.03 | | | |
| | ac | 0.76 | 7.86 | | | |
| | ad | 5.55 | 58.03 | | | |
| | ae | 1.05 | 12.08 | | | |
| | af | 0.68 | 7.05 | | | |
| | ag | 5.84 | 59.06 | | | |
| | ah | 6.79 | 66.02 | | | |
| | ai | 5.05 | 57.09 | | | |
| | aj | 7.35 | 77.24 | | | |
| | ak | 6.84 | 69.13 | | | |
| | al | 1.83 | 14.37 | | | |
| HARVESTING PERIOD | | | | ka | 18.50 | 190.91 |
| | | | | kb | 19.10 | 209.09 |
| | | | | kc | 19.80 | 204.19 |
| | | | | kd | 20.50 | 217.26 |
| | | | | ke | 21.00 | 221.67 |
| | | | | kf | 20.00 | 219.84 |
| | | | | kg | 19.00 | 207.66 |
| | | | | kh | 22.00 | 239.98 |
| | | | | ki | 21.00 | 228.76 |
| | | | | kj | 21.00 | 211.04 |
| | | | | kk | 22.76 | 247.02 |
| | | | | kl | 21.13 | 213.61 |
| | | | | km | 24.72 | 257.47 |
| | | | | kn | 23.72 | 241.66 |
| | | | | ko | 21.98 | 219.65 |
| | | | | kp | 21.49 | 223.38 |
| | | | | kq | 20.49 | 214.75 |
| | | | | kr | 20.66 | 215.51 |
| | | | | ks | 21.67 | 217.63 |
| | | | | kt | 23.07 | 238.96 |
| | | | | ku | 21.75 | 218.39 |
| | | | | kv | 20.48 | 213.06 |
| | | | | kw | 23.62 | 241.08 |
| | | | | kx | 22.57 | 236.78 |
| | | | | ky | 23.60 | 240.83 |

GROWING PERIOD: X(t) AND Y(t)
HARVESTING PERIOD: X(t)
CHEMICAL DATA

FIG. 11C x x : NUMBER OF HARVESTABLE FRUITS, x xi : AVERAGE SIZE OF HARVESTABLE FRUITS, x xii : SIZE DISPERSION, x xiii : NUMBER OF HARVESTS

| VARIABLE / GROWING STATUS | STATUS DATA Y(t) | | | |
|---|---|---|---|---|
| | xx | xxi | xxii | xxiii |
| GROWING PERIOD | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 1 | 5 | 0 | 0 |
| | 2 | 7 | 0 | 0 |
| | 3 | 8 | 0 | 0 |
| | 5 | 8 | 0 | 0 |
| HARVESTING PERIOD | 10 | 10.2 | 1.5 | 1 |
| | 20 | 11.7 | 1.6 | 2 |
| | 25 | 10.3 | 2.0 | 3 |
| | 30 | 11.0 | 1.0 | 5 |
| | 40 | 11.6 | 1.1 | 10 |
| | 50 | 11.1 | 1.4 | 20 |
| | 42 | 12.3 | 1.2 | 25 |
| | 55 | 10.9 | 1.7 | 30 |
| | 60 | 10.7 | 1.8 | 40 |
| | 70 | 14.5 | 1.1 | 50 |
| | 80 | 13.8 | 1.0 | 42 |
| | 70 | 11.9 | 1.9 | 55 |
| | 60 | 14.5 | 1.3 | 60 |
| | 20 | 13.8 | 1.8 | 70 |
| | 10 | 14.0 | 1.0 | 80 |

FIG. 14

| Y(t) | β(ti) | X(ti) | DATA TYPE |
|---|---|---|---|
| AVERAGE SIZE OF FRUITS | 1.5 | CONCENTRATION OF SUBSTANCE α | CHEMICAL DATA |
| | 1 | TEMPERATURE INSIDE HOUSE | CONDITION DATA |
| | −0.5 | HUMIDITY INSIDE HOUSE | CONDITION DATA |
| | 2 | CULTURE SOLUTION AMOUNT | CONDITION DATA |
| | −0.8 | NUMBER OF LEAVES THINNED OUT | CONDITION DATA |

SENSING SYSTEM AND STORAGE MEDIUM STORING DATA STRUCTURE USED IN SENSING SYSTEM

CROSS REFERENCE TO RELATED APPLICATIONS

The present application is a continuation application of International Patent Application No. PCT/JP2020/003441 filed on Jan. 30, 2020, which designated the U.S. and claims the benefit of priority from Japanese Patent Application No. 2019-021776 filed on Feb. 8, 2019. The entire disclosures of all of the above applications are incorporated herein by reference.

TECHNICAL FIELD

The present disclosure relates to a sensing system and a storage medium storing a data structure used in the sensing system.

BACKGROUND

There is proposed a method of identifying a substance or the like as an analysis target with a surface-enhanced Raman Spectroscopy (hereinafter, simply referred to as SERS) method. Specifically, in this method, first, a concavo-convex structure is formed on the surface of the detection substrate, and the analysis target is attached to the portion where the concavo-convex structure is formed. Then, by irradiating the analysis target with a laser beam in this state, the SERS spectrum corresponding to the analysis target is acquired.

SUMMARY

According to an example of the present disclosure, a data structure is provided to be stored in a non-transitory storage medium in a server capable of communicating with a communication terminal used by a user. The data structure includes a processing data and an analysis data. The processing data is relating to a processing condition to form a concavo-convex structure on a detection substrate; the processing data is used to perform a spectroscopic analysis to an analysis target attached to the concavo-convex structure formed on the detection substrate. The analysis data is used to analyze the analysis target from a spectral spectrum of the analysis target obtained by performing the spectroscopic analysis. Herein, the processing data and the analysis data are set for each of a plurality of the analysis targets.

BRIEF DESCRIPTION OF DRAWINGS

The objects, features, and advantages of the present disclosure will become more apparent from the following detailed description made with reference to the accompanying drawings. In the drawings:

FIG. 8A is a diagram showing condition data stored in a storage unit at an early stage of a growing period;

FIG. 9A is a diagram showing condition data stored in a storage unit at a late stage of a growing period;

FIG. 9C is a diagram showing status data stored in a storage unit at a late stage of a growing period;

FIG. 10A is a diagram showing condition data stored in a storage unit during a harvesting period;

FIG. 10C is a diagram showing status data stored in a storage unit during a harvesting period;

FIG. 11A is a diagram showing condition data stored in a storage unit when a harvest period ends;

FIG. 11B is a diagram showing chemical data stored in a storage unit when a harvest period ends;

FIG. 11C is a diagram showing status data stored in a storage unit when a harvest period ends;

FIG. 14 is a diagram showing variables stored in a storage unit according to a third embodiment;

DETAILED DESCRIPTION

Figure 1:
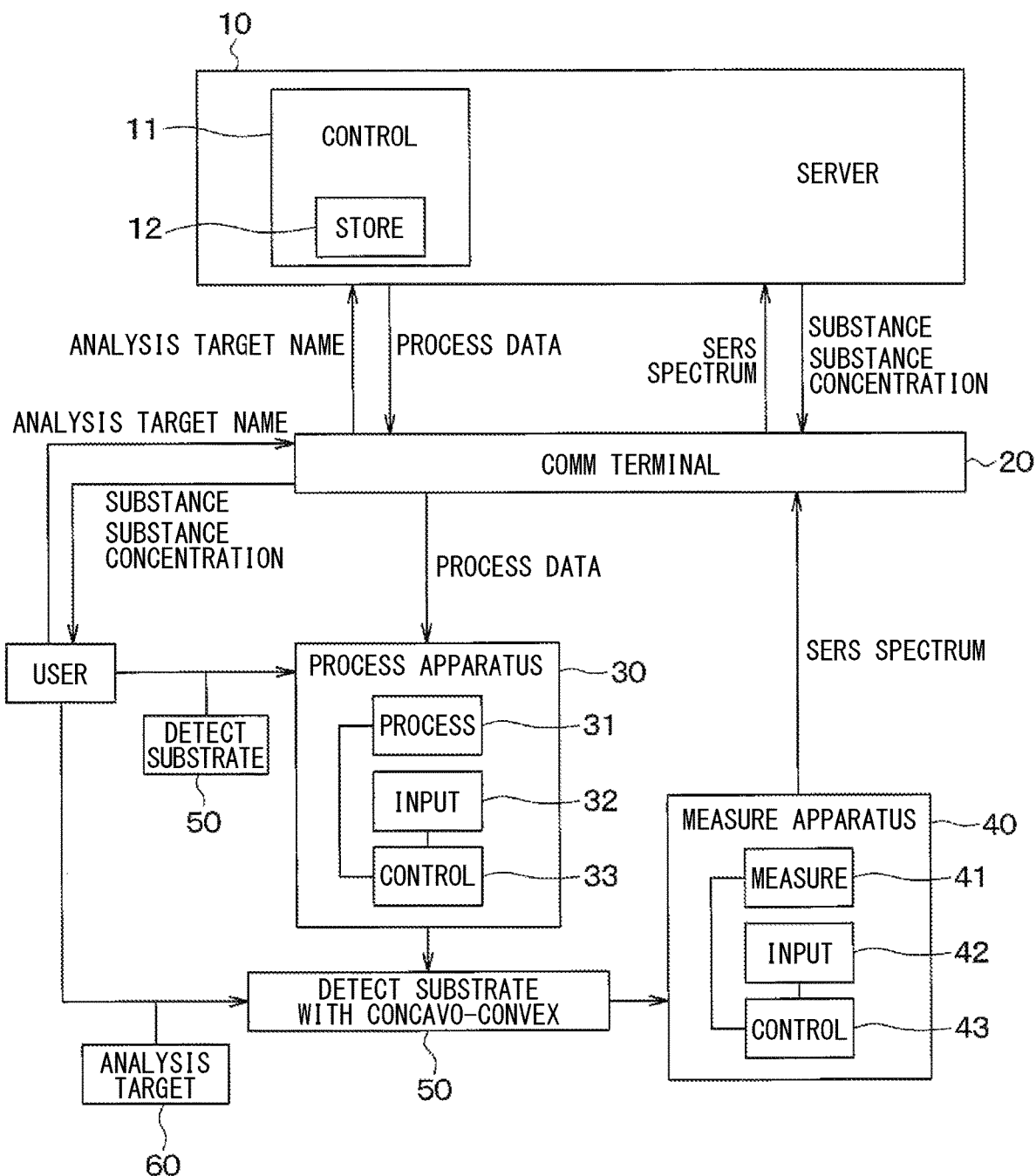
FIG. 1 is a schematic diagram showing a configuration of a sensing system according to a first embodiment.

Hereinafter, embodiments of the present disclosure will be described with reference to the drawings. In each of the following embodiments, parts that are the same or equal to each other will be described with the same reference numerals.

First Embodiment

A sensing system according to a first embodiment will be described with reference to the drawings. The sensing system of the present embodiment is preferably used for a user to investigate a substance name, substance concentration, etc. of an analysis target. Although the sensing system of this embodiment will be described in detail later, it uses the SERS method to notify the user of the substance name and substance concentration of the analysis target from the analysis result based on the SERS spectrum.

First, the configuration of the sensing system of the present embodiment will be described. As shown in FIG. 1, the sensing system includes a server 10, a communication terminal 20, a processing apparatus 30, and a measuring apparatus 40.

The server 10 is configured to include (i) a controller unit 11 and (ii) a communicator unit (not shown) configured to be able to transmit and receive various data with the communication terminal 20. The server 10 of the present embodiment is configured to be capable of wireless communication with the communication terminal 20.

The controller unit 11, which may also referred to as a controller, includes a microcomputer having a CPU and a storage unit 12. The storage unit 12, which may also referred to as a storage, includes a non-transitory tangible storage media such as ROM, RAM, flash memory, and HDD. Here, CPU is an abbreviation for Central Processing Unit, ROM is an abbreviation for Read Only Memory, RAM is an abbreviation for Random Access Memory, and HDD is an abbreviation for Hard Disk Drive.

Figure 2:
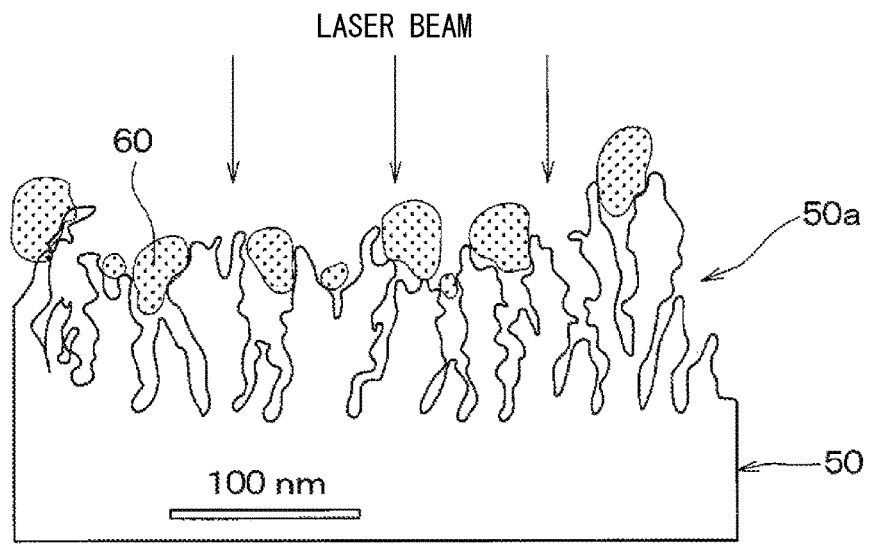
FIG. 2 is a diagram for explaining a SERS method.

Here, the sensing system of the present embodiment uses the SERS method as described above. As shown in FIG. 2, the SERS method is a method in which (i) an analysis target 60 is attached to a detection substrate 50 on which a concavo-convex structure 50a having nano-concavities and convexities is formed, (ii) a laser beam is radiated to the analysis target 60 attached to the detection substrate 50, and (iii) a SERS spectrum is acquired based on the generated scattered light. The concavo-convex structure 50a is formed to amplify the scattered light (that is, the detection signal). Note that, in the SERS method, the detection sensitivity changes depending on the relationship between the concavo-convex structure 50a of the detection substrate 50 and the analysis target 60. Therefore, in order to obtain an appropriate SERS spectrum by the SERS method, it is preferable that the concave-convex structure 50a of the detection substrate 50 has a shape corresponding to the analysis target 60.

Therefore, (i) various substances and (ii) processing data regarding processing conditions for forming the concavo-convex structure 50a suitable for these substances on the detection substrate 50 are stored in association with each other in the storage unit 12. Further, in the storage unit 12, names, trade names, and the like are also stored in association with various substances. For example, in the case of tomato, substances such as sodium, potassium, calcium, vitamins, carotene, and fatty acids contained in tomato are stored in association with tomato as the analysis target 60. Therefore, it can be said that the storage unit 12 stores the processing data of the concavo-convex structure 50a suitable for the analysis target 60. Further, since the concavo-convex structure 50a suitable for each substance changes depending on the material of the detection substrate 50, the material of the detection substrate 50 is also stored in association with the various substances and the processing data in the storage unit 12.

In this embodiment, as will be described later, the concavo-convex structure 50a is formed on the substrate 50 by radiating the laser beam. Therefore, the storage unit 12 stores the processing conditions for radiating the laser beam as the processing data, for example, the intensity, wavelength, irradiation spot, and the like of the laser beam.

Further, the storage unit 12 stores analysis data of SERS spectra related to various substances. That is, the storage unit 12 stores the master spectrum for analysis.

Then, the controller unit 11 realizes various control operations by the CPU reading various data from the storage unit 12 and executing the data. Specifically, when the controller unit 11 receives the data related to the detection substrate 50 and the analysis target 60 from the communication terminal 20, it determines that the signal requesting the processing data has been received, and transmits the processing data related to the processing conditions to the communication terminal 20. In the present embodiment, when the analysis target 60 contains a plurality of substances, the processing data for forming the concavo-convex structure 50a suitable for each substance is transmitted to the communication terminal 20, respectively.

Figure 3:
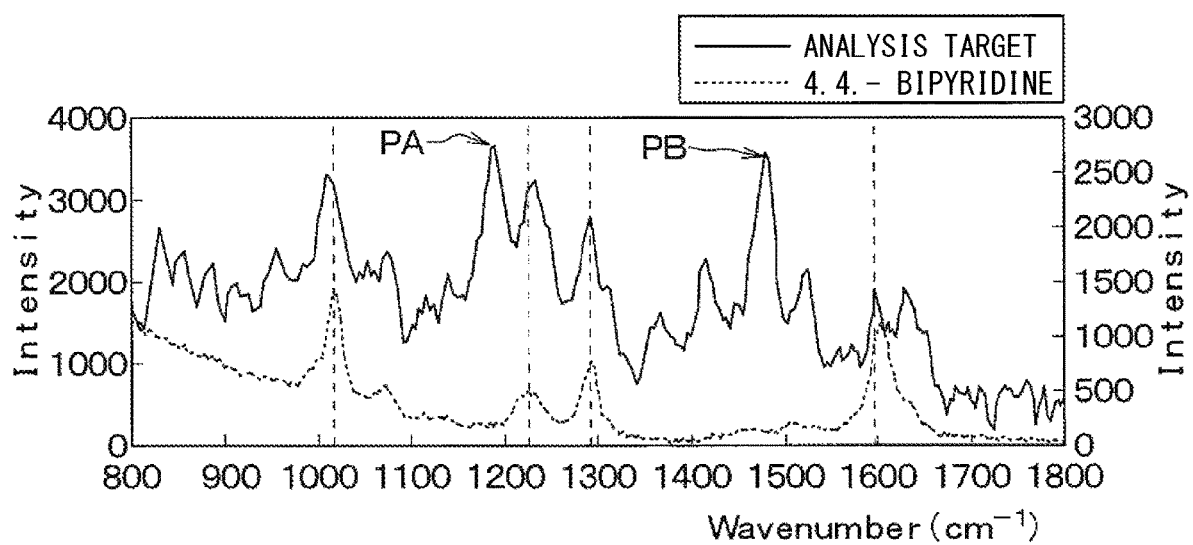
FIG. 3 is a diagram showing a SERS spectrum of an analysis target and a SERS spectrum for analysis.

When the controller unit 11 receives the SERS spectrum from the communication terminal 20, the controller unit 11 analyzes the substance name and the substance concentration contained in the analysis target 60 using the analysis data from the received SERS spectrum, and transmits the analysis result to the communication terminal 20. For example, FIG. 3 is a diagram showing (i) the SERS spectrum of the analysis target 60 obtained after applying the 4,4-bipyridine solution to the surface of the tomato and wiping it off, and (ii) the SERS spectrum of 4,4-bipyridine as analysis data. In FIG. 3, the vertical axis on the left side is a value indicating the strength of the analysis target 60, and the vertical axis on the right side is a value indicating the strength of the analysis data.

As shown in FIG. 3, the SERS spectrum of the analysis target 60 is a waveform having peaks at different wave numbers while reproducing the main peaks of 4,4-bipyridine at the positions of the wave numbers shown by the dotted lines in FIG. 3. That is, in FIG. 3, peak PA, peak PB, etc. show (i) components contained in tomatoes different from 4,4-bipyridine, (ii) components contained in pesticides attached to tomatoes, and (iii) the like. Therefore, the controller unit 11 analyzes (i) the substance corresponding to the peak PA and the peak PB and (ii) the substance concentration with reference to the analysis data of each substance stored in the storage unit 12. The controller unit 11 analyzes the substance concentration based on the intensity of the peak.

Although not shown in particular, the communication terminal 20 is configured to include a communication unit configured to be able to communicate various data with the server 10, a controller unit that performs predetermined processing, and the like. For example, the communication terminal 20 is provided to be a smartphone, a tablet terminal, a personal computer, etc.

The processing apparatus 30 is an apparatus for processing the detection substrate 50 used in the SERS method, and is configured to include a processing unit 31, an input unit 32, and a controller unit 33, which may also referred to as a controller. Further, although not particularly shown, the processing apparatus 30 also has a communication unit and the like capable of transmitting and receiving various data to and from the communication terminal 20. The processing apparatus 30 of the present embodiment may be configured to be capable of wireless communication with the communication terminal 20, or may be configured to be capable of wired communication.

Figure 4:
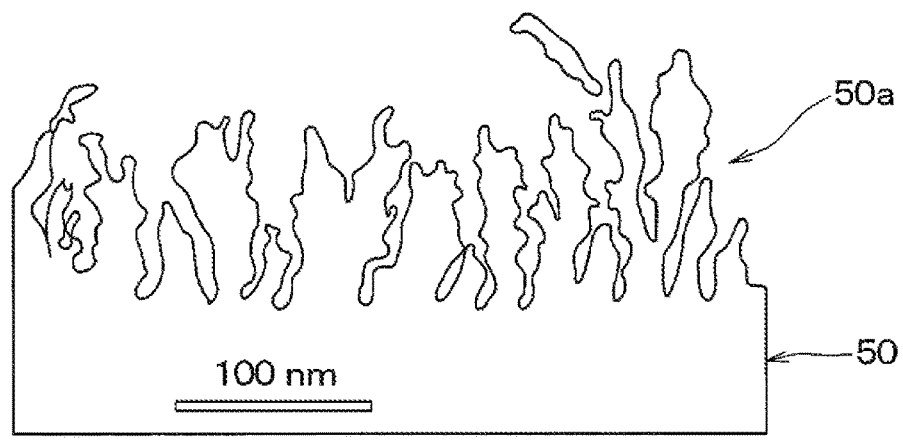
FIG. 4 is a diagram showing a concave-convex structure of a detection substrate.

In the present embodiment, the processing unit 31 includes a pedestal for fixing the detection substrate 50, a laser radiation unit for radiating a laser beam, and the like. Then, the processing unit 31 radiates the laser beam to form the detection substrate 50 for the SERS method in which the concavo-convex structure 50a having nano-concavities and convexities is formed, as shown in FIG. 4. Specifically, the processing unit 31 radiates the laser beam, melts the surface of the detection substrate 50 and scatters the substance, and redeposits the scattered substance to build the substrate 50 on which the concavo-convex structure 50a having nano-concavities and convexities is formed.

Although FIG. 4 shows a concavo-convex structure 50a having nano-concavities and convexities of about several nanometers, the concavo-convex structure 50a may have a configuration having smaller nano-concavities and convexities, or a configuration having even larger nano-concavities and convexities. The detection substrate 50 is made of a metal material such as gold, silver, nickel, cobalt, copper, aluminum, or titanium. Further, the detection substrate 50 is prepared by forming, for example, a gold-plated, silver-plated, nickel-plated, cobalt-plated film or the like on a substrate made of silicon, glass, a rubber sheet or the like.

The input unit 32 includes a touch panel or the like that can be operated by the user.

The controller unit 33 includes a microcomputer connected with the processing unit 31 and the input unit 32. The microcomputer includes a CPU (not shown) and a storage unit composed of a non-transitory tangible storage medium such as a ROM, a RAM, a flash memory, or an HDD. Then, the controller unit 33 realizes various control operations by the CPU reading various data from the storage unit 12 and executing the data.

Figure 5:
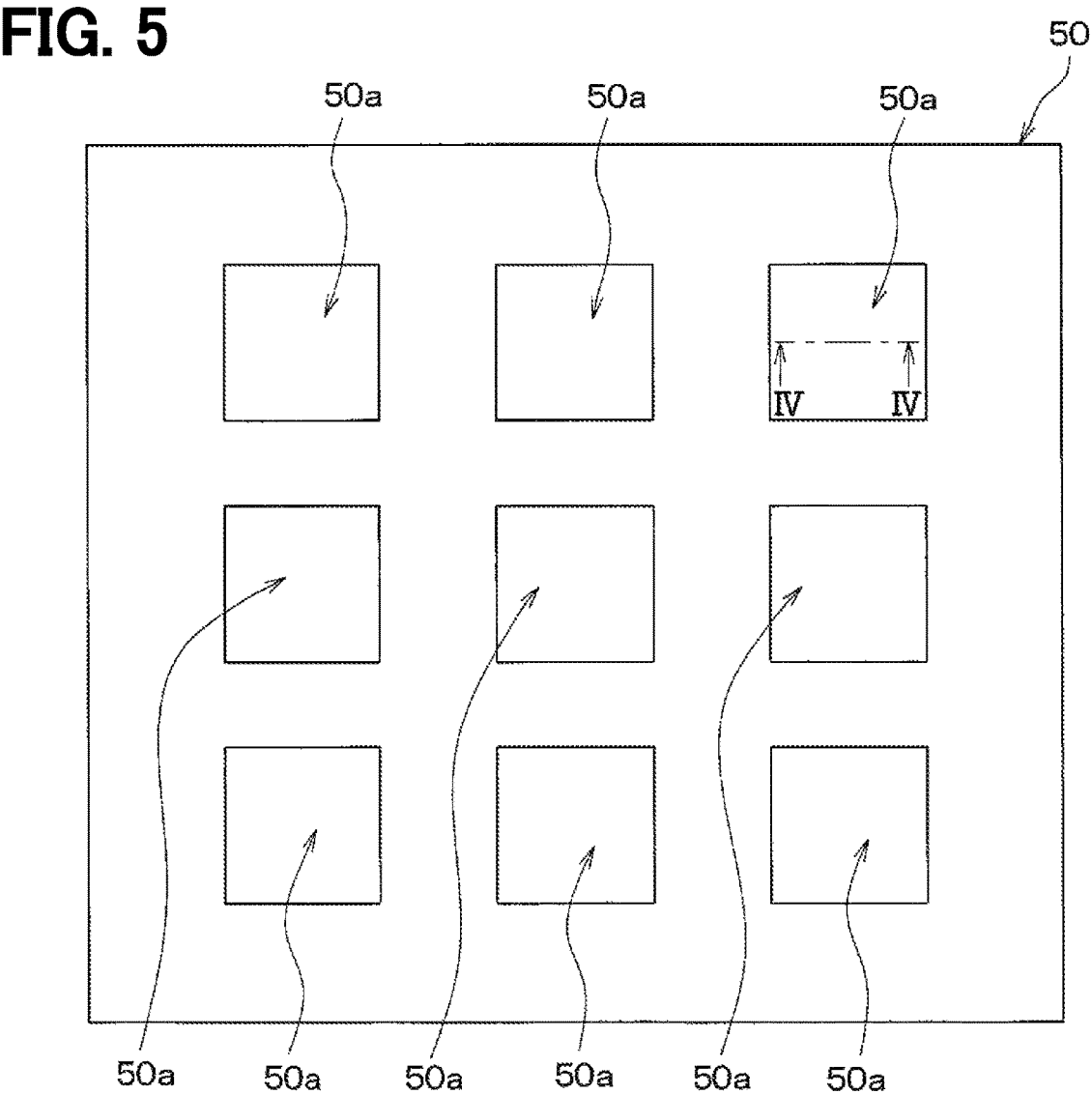
FIG. 5 is a plan view of a detection substrate.

Specifically, the controller unit 33 receives the processing data from the communication terminal 20. When the input unit 32 is operated by the user so as to start the processing, the controller unit 33 controls the processing unit 31 based on the processing data. The detection substrate 50 having the concavo-convex structure 50a is thereby built or formed. In this case, in the present embodiment, when the analysis target 60 contains a plurality of substances, the server 10 transmits the processing data for forming the concavo-convex structure 50a suitable for each substance to the communication terminal 20. That is, a plurality of processing data are transmitted from the server 10 to the communication terminal 20. Therefore, when a plurality of processing data is transmitted from the server 10 to the communication terminal 20, a detection substrate 50 having a plurality of concavo-convex structures 50a is prepared as shown in FIG. 5. Note that FIG. 4 is also a diagram corresponding to the IV-IV cross section in FIG. 5.

The measuring apparatus 40 is an apparatus that detects the SERS spectrum by the SERS method, and has a configuration including a measuring unit 41, an input unit 42, and a controller unit 43, which may also referred to as a controller. Further, although not particularly shown, the measuring apparatus 40 also includes a communication unit and the like capable of transmitting and receiving various data to and from the communication terminal 20. The measuring apparatus 40 of the present embodiment may be configured to be capable of wireless communication with the communication terminal 20, or may be configured to be capable of wired communication.

In the present embodiment, the measuring unit 41 includes a pedestal for fixing the detection substrate 50, a laser radiation unit for radiating a laser beam, a detection unit for generating a SERS spectrum by detecting and analyzing scattered light, and the like.

The input unit 42 includes a touch panel or the like that can be operated by a user.

The controller unit 43 includes a microcomputer connected with the measuring unit 41 and the input unit 42. The microcomputer includes a CPU (not shown) and a storage unit 12 composed of a non-transitory tangible storage medium such as a ROM, a RAM, a flash memory, or an HDD. Then, the detection substrate 50 to which the analysis target 60 is attached is arranged in the measuring unit 41 and the input unit 42 is operated so that the user starts the measurement. The controller unit 43 then controls the measuring unit 41 to thereby detect the SERS spectrum. Then, the controller unit 43 transmits the detected SERS spectrum to the communication terminal 20.

In the present embodiment, the server 10, the processing apparatus 30, and the measuring apparatus 40 can transmit and receive data via the communication terminal 20. That is, the direct communication between the server 10, the processing apparatus 30, and the measuring apparatus 40 is disabled. In other words, the server 10 cannot directly control the processing apparatus 30 and the measuring apparatus 40.

The above is the configuration of the sensing system in this embodiment. The processing apparatus 30 and the measuring apparatus 40 may be owned by the user himself/herself, or may be installed in a facility such as a convenience store or a supermarket so that users can use them in these facilities. When the processing apparatus 30 is installed in a facility or the like, a worker who is familiar with the configuration of the processing apparatus 30 or the like may be assigned, and the user may outsource or entrust the processing to the worker. Similarly, when the measuring apparatus 40 is installed in a facility or the like, a worker who is familiar with the configuration of the measuring apparatus 40 or the like may be assigned, and the user may outsource or entrust the measurement to the worker. Further, the detection board 50 may be sold to the user by, for example, the owner of the server 10 or a related person, or may be distributed to the user by the owner of the server 10 or a related person.

Figure 6:
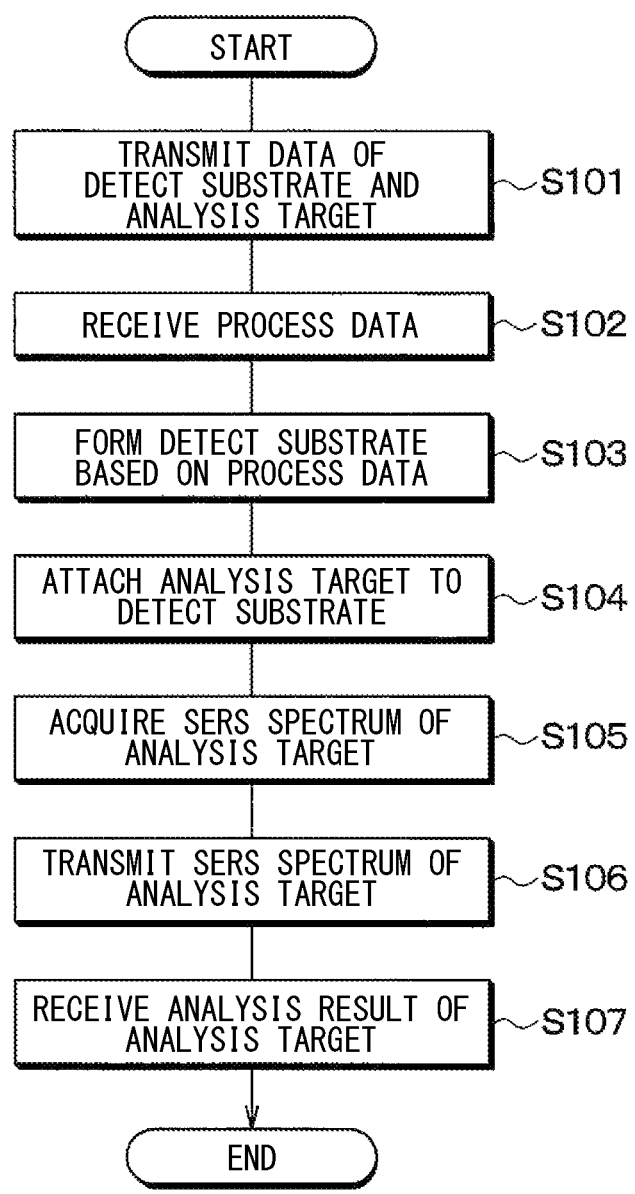
FIG. 6 is a flowchart showing an operation performed by a user.

Next, a method in which the user analyzes the analysis target 60 using the sensing system will be described with reference to FIGS. 1 and 6.

First, in step S101, the user transmits data regarding the detection substrate 50 and the analysis target 60 from the communication terminal 20 to the server 10. At this time, the user transmits the material of the detection substrate 50 and the like as the data of the detection substrate 50. In addition, the user transmits the name, trade name, and the like as the data of the analysis target 60. For example, when the analysis target 60 is a tomato which is an agricultural product, the tomato or the trade name of the tomato is transmitted.

Next, in step S102, the user transmits various data to the server 10 in step S101, so that the processing data related to the processing conditions of the detection substrate 50 is transmitted from the server 10. The processing data is received by the communication terminal 20. In this embodiment, since the detection substrate 50 is processed by using the processing apparatus 30, the received processing data includes various data such as laser beam intensity, wavelength, spot system, and energy.

Subsequently, in step S103, the user forms the concavo-convex structure 50a on the detection substrate 50 based on the processing data received in step S102. Specifically, the user prepares the detection substrate 50, arranges the detection substrate 50 in the processing apparatus 30, and transmits the processing data received in step S102 to the processing apparatus 30. Then, by operating the input unit 32 in the processing apparatus 30, the detection substrate 50 having the concavo-convex structure 50a based on the processing data is built. At this time, when a plurality of substances are contained in the analysis target 60, a detection substrate 50 having a plurality of concavo-convex structures 50a is formed as shown in FIG. 5.

Next, in step S104, the user attaches the analysis target 60 to the portion of the detection substrate 50 on which the concavo-convex structure 50a is formed. The method by which the user attaches the analysis target 60 to the detection substrate 50 can be appropriately changed. For example, when the analysis target 60 is an agricultural product such as tomato, the user attaches the analysis target 60 to the portion where the concavo-convex structure 50a is formed by pressing the detection substrate 50 against the surface of the agricultural product. Further, for example, when the analysis target 60 is an agricultural product such as tomato, the user attaches the analysis target 60 to the portion where the concavo-convex structure 50*a* is formed by grinding the analysis target 60 and applying it to the detection substrate 50. In this case, when a plurality of concave-convex structures 50*a* are formed on the detection substrate 50, the user attaches the analysis target 60 to each of the concave-convex structures 50*a*.

Then, in step S105, the user acquires the SERS spectrum of the analysis target 60. Specifically, the user arranges the detection substrate 50, which the analysis target 60 is attached to, on the measuring apparatus 40, and acquires the SERS spectrum by operating the input unit 42. When a plurality of concavo-convex structures 50*a* are formed on the detection substrate 50, the SERS spectrum of the analysis target 60 formed on each concavo-convex structure 50*a* is detected.

Next, in step S106, the user receives the SERS spectrum of the analysis target 60 from the measuring apparatus 40 by the communication terminal 20, and transmits the received SERS spectrum to the server 10. As a result, the server 10 analyzes the substance, the substance concentration, and the like contained in the analysis target 60 from the transmitted SERS spectrum, and transmits the analysis result to the communication terminal 20.

Then, in step S107, the user acquires the analysis result from the server 10. As a result, the user can acquire the substance and the substance concentration of the analysis target 60.

Figure 7:
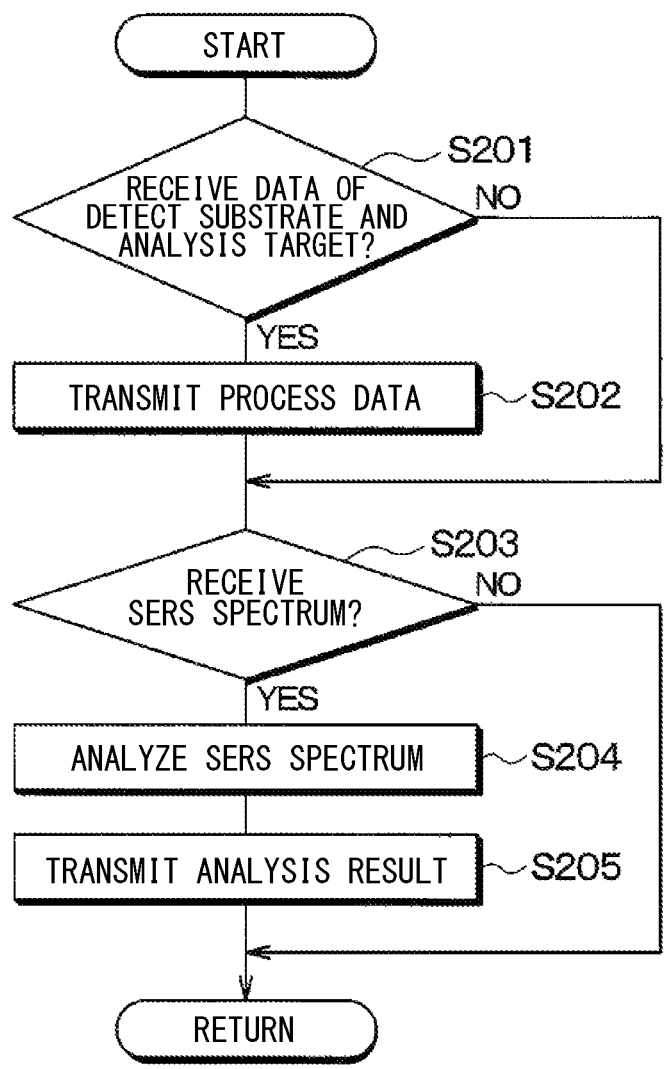
FIG. 7 is a flowchart showing an operation executed by a controller unit in a server.

Next, the operation executed by the controller unit 11 of the server 10 in the sensing system of the present embodiment will be described with reference to FIGS. 1 and 7.

First, in step S201, the controller unit 11 determines whether or not the data of the detection substrate 50 and the analysis target 60 are received. Then, when the controller unit 11 determines that the data of the detection board 50 and the analysis target 60 is received (that is, step S201: YES), the controller unit 11 transmits the processing data regarding the processing conditions of the detection substrate 50 suitable for the received detection substrate 50 and the analysis target 60. In this case, when the analysis target 60 contains a plurality of substances, the processing data regarding the processing conditions of the detection substrate 50 suitable for each substance is transmitted.

After transmitting the processing data or when determining that the data of the detection substrate 50 and the analysis target 60 is not received (that is, step S201: NO), the controller unit 11 advances the process to step S203. In step S203, the controller unit 11 determines whether or not the SERS spectrum is received. Then, when the controller unit 11 determines that the SERS spectrum is received (that is, step S203: YES), the controller unit 11 analyzes the received SERS spectrum in step S204 to specify the substance and the substance concentration. Specifically, the controller unit 11 specifies the substance and the substance concentration contained in the analysis target 60 by comparing the SERS spectrum with the analysis data of each substance.

Then, in step S205, the controller unit 11 transmits data related to the analysis result to the communication terminal 20.

As described above, in the sensing system of the present embodiment, when the server 10 receives the signal requesting the processing data, the server 10 transmits the processing data. When the SERS spectrum is received, the substance and the substance concentration contained in the server 10 are analyzed. The analysis result is then transmitted. Therefore, the user can easily acquire the processing data for building or preparing the detection substrate 50 having the concavo-convex structure 50*a* suitable for the analysis target 60 from the server 10. Further, the user can easily specify the substance or the like of the analysis target 60 by transmitting the SERS spectrum to the server 10. Therefore, the user can easily investigate the analysis target 60 that he/she wants to investigate.

Further, since the user only needs to prepare the detection substrate 50 having the concavo-convex structure 50*a* immediately before the analysis, the user does not have to store the detection substrate 50 on which the concave-convex structure 50*a* is formed. Therefore, it is possible to prevent the detection substrate 50 from deteriorating with storage.

Then, the processing apparatus 30 radiates the laser beam to form the concavo-convex structure 50*a* on the detection substrate 50. Therefore, in particular, when a plurality of concave-convex structures 50*a* are formed on the detection substrate 50, the concave-convex structure 50*a* can be easily formed locally, and the configuration of each concave-convex structure 50*a* can be easily changed by changing the irradiation conditions of the laser beam.

Further, the measuring apparatus 40 detects the SERS spectrum by the SERS method. Therefore, glass or the like can be used as the detection substrate 50, and the selectivity of the detection substrate 50 can be improved.

Further, the server 10, the processing apparatus 30, and the measuring apparatus 40 can communicate data with each other via the communication terminal 20. That is, the direct communication between the server 10, the processing apparatus 30, and the measuring apparatus 40 is prohibited or disabled. Therefore, as compared with the case where the server 10, the processing apparatus 30, and the measuring apparatus 40 are capable of the direct communication with each other, it is possible to make it difficult for the server 10 to perform an unauthorized operation on the processing apparatus 30 and the measuring apparatus 40.

Modified Example of First Embodiment

In the first embodiment, the example in which the analysis target 60 is an agricultural product has been described, but the analysis target 60 may be a livestock product, a marine product, or a forest product. That is, agriculture, forestry, and fishery products can be applied as the analysis target 60. Further, the analysis target 60 may be an industrial product such as a semiconductor device or an in-vehicle component. In this case, for example, the life of the product can be estimated by detecting a component or the like attached to the surface of the industrial product. Further, the analysis target 60 may be fine particles or the like in a gas generated in a manufacturing process for manufacturing an industrial product. Further, the analysis target 60 may be a gas, fine particles, or the like existing in a predetermined space such as a vehicle space. When such fine particles are attached to the detection substrate 50, the detection substrate 50 may be exposed to a place where the fine particles can exist.

Second Embodiment

A second embodiment will be described. In this embodiment, the controller unit 11 of the server 10 predicts the future result as compared with the first embodiment. Others are the same as those in the first embodiment. In this embodiment, an example in which the farm worker as a user applies the present sensing system to predict the yield of fruits as an agricultural product will be described.

In the following, an example of cultivating fruits in a plastic greenhouse will be described. In the following, the period during which the fruit can be harvested is defined as a harvesting period, and the period from the start of cultivating the fruit to the start of the harvesting period is defined as a growing period.

In the present embodiment, various data are stored in the storage unit 12 in the server 10, as shown in FIGS. 8A, 8B, 8C, 9A, 9B, 9C, 10A, 10B, 10C, 11A, 11B, and 11C.

Specifically, a growing period and a harvesting period are set in the storage unit 12. Then, as shown in FIGS. 8A, 9A, 10A, and 11A, the condition data regarding the fruit cultivation conditions are stored in order. Further, as shown in FIGS. 8B, 9B, 10B, and 11B, the storage unit 12 stores chemical data related to the SERS spectrum in order. Further, as shown in FIGS. 8C, 9C, 10C, and 11C, the storage unit 12 stores status data regarding the status of the fruit in order. The condition data, the chemical data, and the status data are stored in association with each other. That is, for example, in the conditional data, the data in the first row in the growing period is the data related to Oct. 22, 2018. Similarly, in the chemical data and status data, the data in the first row in the growing period is also the data stored on Oct. 22, 2018. In other words, the data for each row is the data stored on the same day and is time-related data or temporally related data.

In this embodiment, the storage unit 12 stores the condition data. The condition data includes the date and time, the temperature outside the house, the humidity outside the house, the air volume, the amount of solar radiation, the temperature inside the house, the humidity inside the house, the culture solution concentration, the culture solution amount, the number of leaves thinned out, the number of leaves, the average stem thickness, and the stem height. However, the house here is a vinyl house. The condition data is data that affects the fruit when the fruit is cultivated, and can be said to be data different from the chemical data described later.

Further, the storage unit 12 stores the chemical data. The chemical data includes the leaf SERS spectrum shape, the leaf SERS spectrum peak height of substance α, the leaf concentration of substance α, the fruit SERS spectrum shape, the fruit SERS spectrum peak height of substance β, and the concentration of substance β contained in fruits. It can be said that the chemical data is data based on the SERS spectrum or data obtained from the SERS spectrum. Further, in FIGS. 8B, 9B, 10B, and 11B, the concentration of the substance α contained in the leaves is simply indicated as the concentration of the substance α, and the concentration of the substance β contained in the fruit is simply indicated as the concentration of the substance β.

The data relating to the leaf SERS spectrum shape here is data that stores the shape of the SERS spectrum itself, and is shown in each diagram by using alphabets for convenience. Further, the peak height of each substance in the SERS spectrum is the height of the peak indicating a predetermined substance analyzed from the SERS spectrum. Here, for example, for leaves, an example in which the peak height of the predetermined substance α and the concentration of the predetermined substance α are stored in the storage unit 12 will be described, but the peak heights and concentrations of a plurality of substances may be stored in the storage unit 12. Similarly, for fruits, an example in which the peak height of the predetermined substance β and the concentration of the predetermined substance β are stored in the storage unit 12 will be described, but the peak heights and concentrations of a plurality of substances may be stored in the storage unit 12.

Further, the storage unit 12 stores the status data. The status data includes the number of harvestable fruits, the average size of harvestable fruits, the size dispersion, and the number of harvests. It should be noted that the status data is different from the chemical data and can be said to be data showing the fruit status itself.

Then, as will be described later, the condition data and the status data are stored in the storage unit 12 by transmitting the numerical values actually measured by the farm worker from the communication terminal 20 to the server 10. The chemical data is stored in the storage unit 12 by (i) the farm worker measuring the SERS spectrum and transmitting the SERS spectrum to the server 10, and (ii) the server 10 analyzing the transmitted SERS spectrum and storing it in the storage unit 12.

When the controller unit 11 of the present embodiment receives the various data, the controller unit 11 stores the various data in the storage unit 12. Further, when the controller unit 11 receives the prediction start signal from the farm worker via the communication terminal 20, the controller unit 11 performs the multiple regression analysis shown in the following equation using at least the condition data and the chemical data stored in the storage unit 12, and predicts the future outcome or result. That is, the controller unit 11 predicts the future outcome or result by performing multiple regression analysis that predicts one objective variable with a plurality of explanatory variables.

$$Y(t) = \sum_i \beta(t_i) \cdot X(t_i) \qquad \text{[Expression 1]}$$

In Expression 1, X (ti) is an explanatory variable, Y (t) is an objective variable, and β(ti) is a partial regression coefficient. Then, the controller unit 11 calculates the partial regression coefficient β (ti) from the explanatory variable X (ti) and the objective variable Y (t), and predicts what value the objective variable Y (t) will be when the explanatory variable X (ti) changes.

Figure 8B:
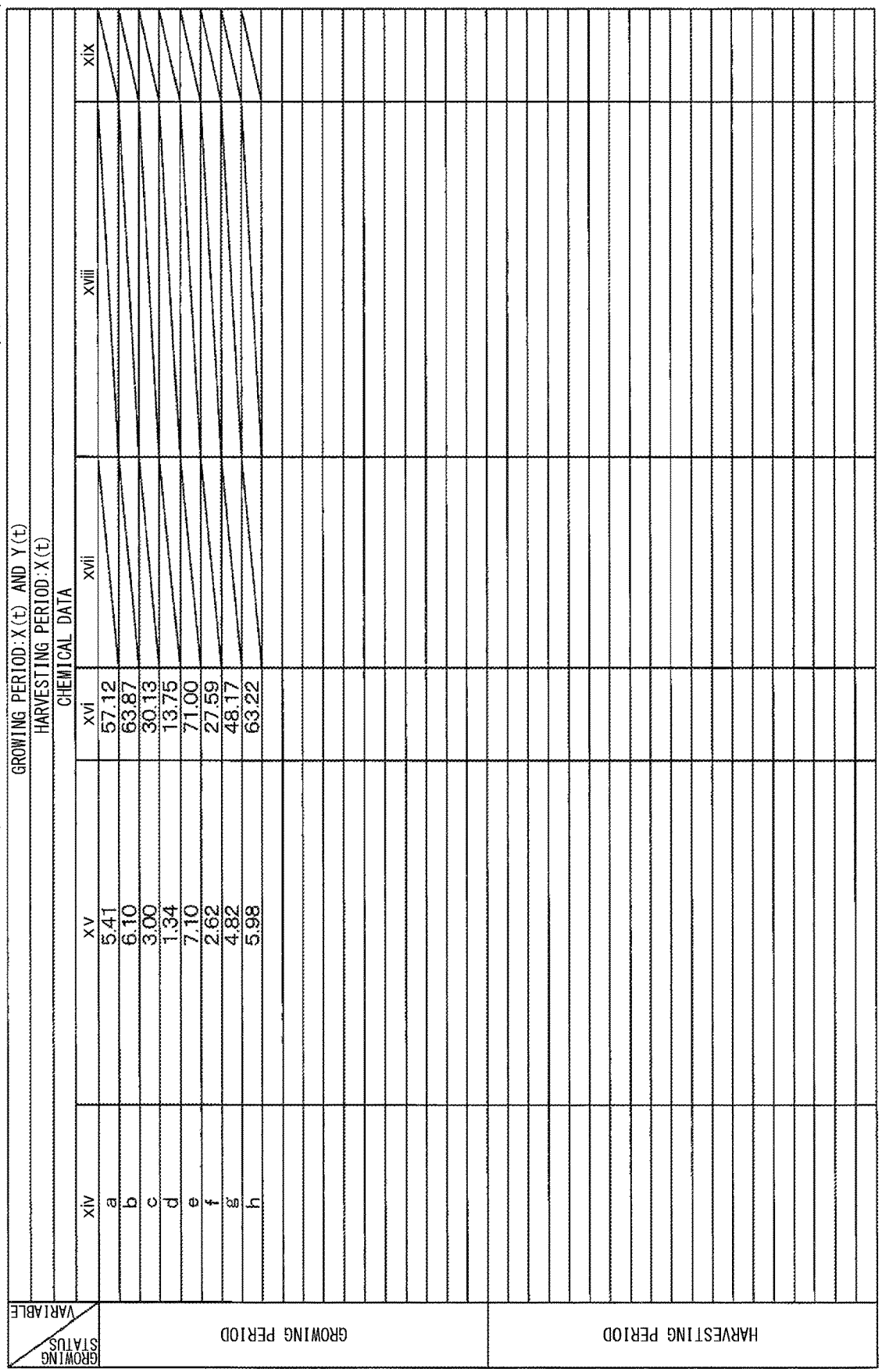
FIG. 8B is a diagram showing chemical data stored in a storage unit at an early stage of a growing period.
Figure 8C:
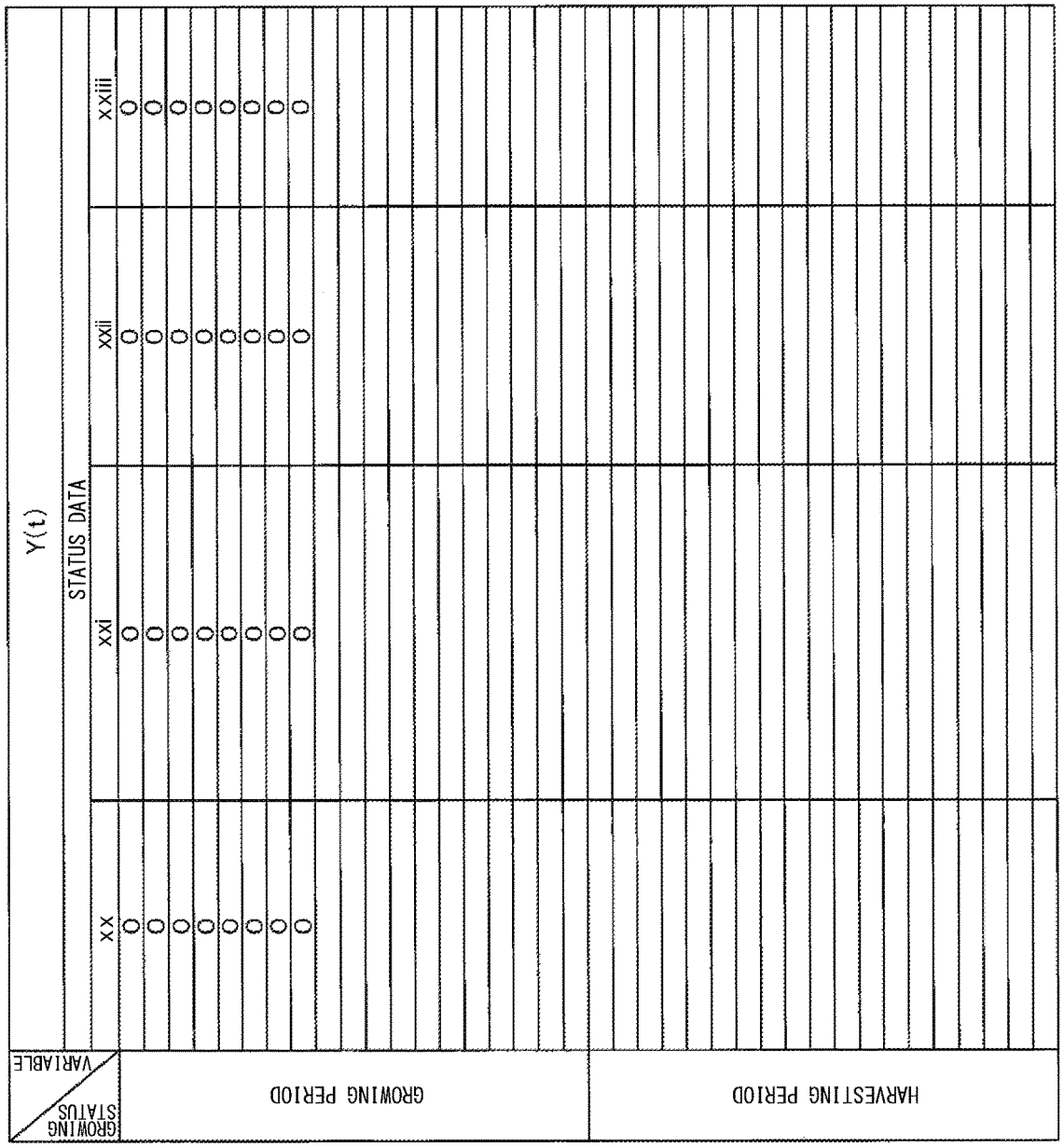
FIG. 8C is a diagram showing status data stored in a storage unit at an early stage of a growing period.

For example, if empirically the number of leaves during the growing period has a large effect on the final number of harvestable fruits, the farm worker may want to predict the number of leaves at a later date, during the growing period. In this case, suppose the case where the controller unit 11 receives the prediction start signal for predicting the number of leaves under the state where the data shown in FIGS. 8A to 8C are stored. In this case, the controller unit 11 predicts the number of leaves with Y (t) as the number of leaves and X (t) as the date and time, the temperature outside the house, the humidity outside the house, the air volume, the amount of solar radiation, the temperature inside the house, the humidity inside the house, the culture solution concentration, the culture solution amount, the number of leaves thinned out, the number of leaves, the average stem thickness, the stem height, the shape of the leaf SERS spectrum, the peak height of the substance α in the leaf SERS spectrum, and the concentration of the substance α contained in the leaf. That is, the controller unit 11 predicts the number of leaves using the condition data and the chemical data.

Figure 9B:
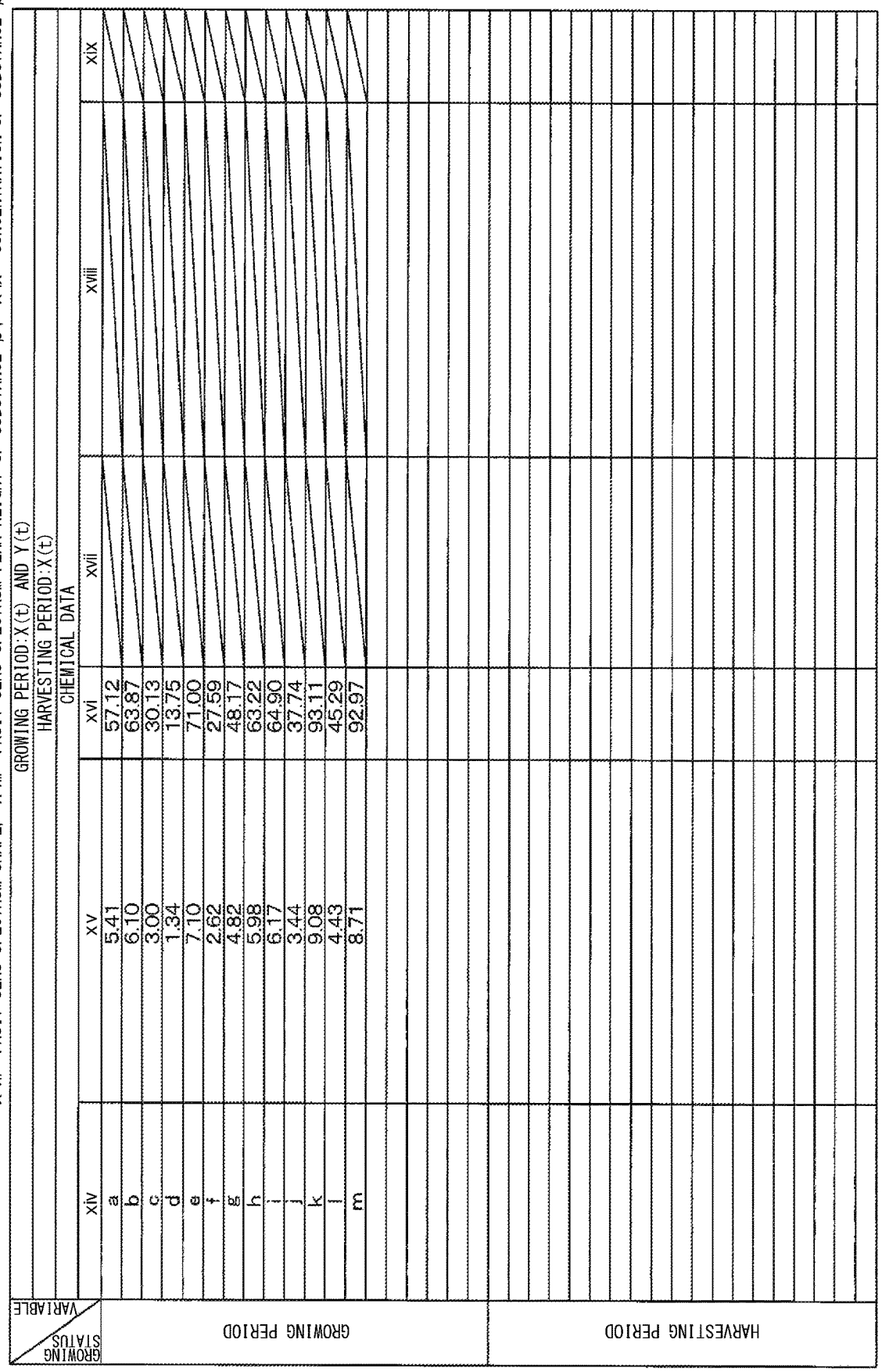
FIG. 9B is a diagram showing chemical data stored in a storage unit at a late stage of a growth period.

Furthermore, even before the harvest period, depending on the fruit, if sufficient leaf and stem data are accumulated, it may be possible to predict the number of harvestable fruits at a later date. Suppose the case where the controller unit 11 receives the prediction start signal for predicting the number of harvestable fruits even before the harvest period, X is stored under the state where the data shown in FIGS. 9A to 9C is stored. In this case, the controller unit 11 predicts the number of fruits with Y (t) as the number of fruits that can be harvested, and X (t) as the date and time, the temperature outside the house, the humidity outside the house, the air volume, the amount of solar radiation, the temperature inside the house, the humidity inside the house, the culture solution concentration, the culture solution amount, the number of leaves thinned out, the number of leaves, the average stem thickness, the stem height, the shape of the leaf SERS spectrum, the peak height of the substance α in the leaf SERS spectrum, and the concentration of the substance α contained in the leaf. That is, the controller unit 11 predicts the number of fruits that can be harvested using the condition data and the chemical data. In this embodiment, the number of harvestable fruits corresponds to the yield.

Figure 10B:
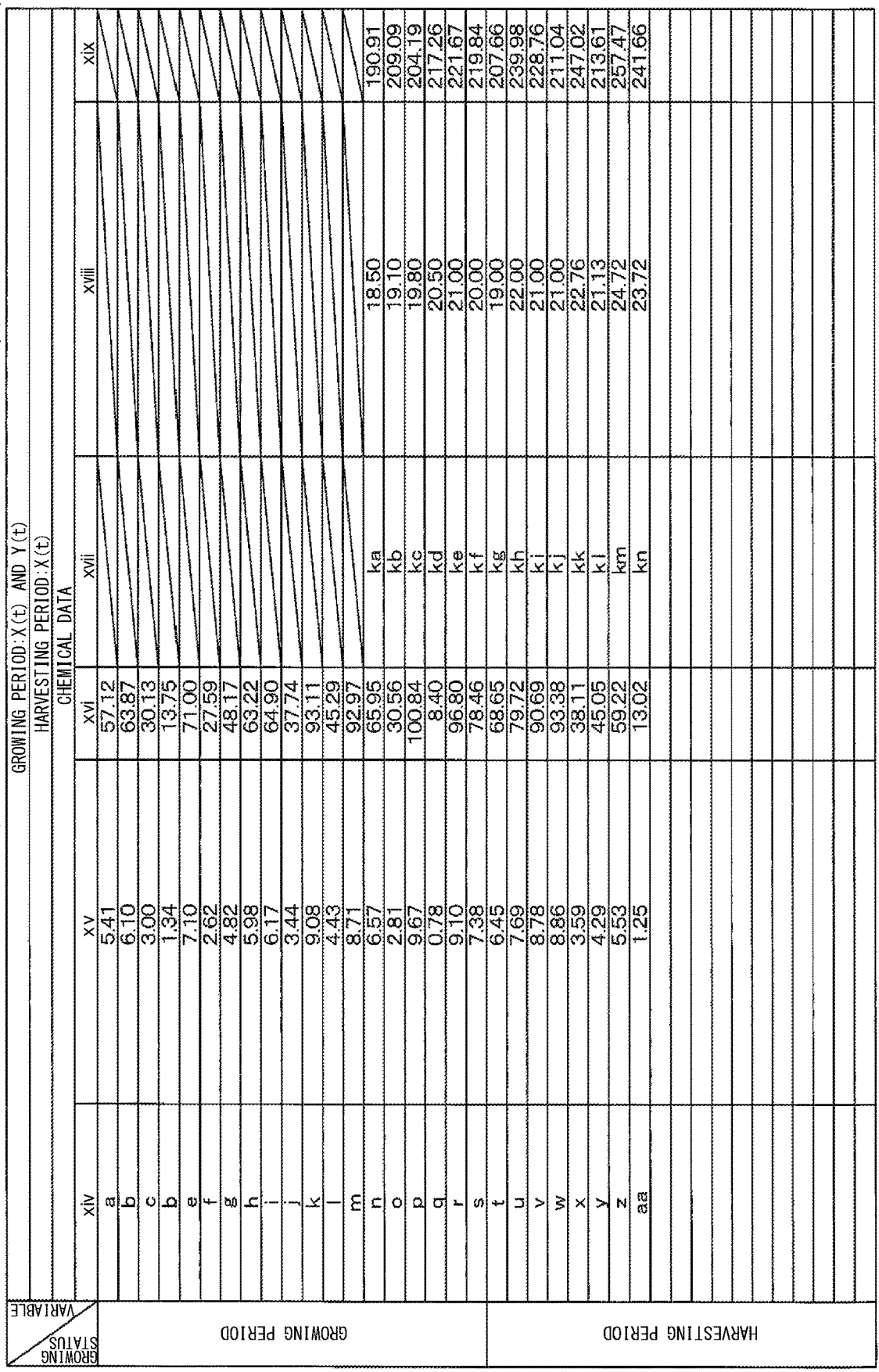
FIG. 10B is a diagram showing chemical data stored in a storage unit during a harvesting period.

In addition, farm workers may want to predict the number of fruits that can be harvested at a later date, during the harvest period. In this case, when the controller unit 11 receives the prediction start signal for predicting the number of harvestable fruits under the state where the data shown in FIGS. 10A to 10C is stored, the controller unit 11 predicts the number of fruits with Y (t) as the number of harvestable fruits and the X (t) as the date and time, the temperature outside the house, the humidity outside the house, the air volume, the amount of solar radiation, the temperature inside the house, the humidity inside the house, the culture solution concentration, the culture solution amount, the number of leaves thinned out, the number of leaves, the average stem thickness, the stem height, the leaf SERS spectrum shape, the leaf SERS spectrum peak height of substance α, the leaf concentration of substance α, the fruit SERS spectrum shape, the fruit SERS spectrum peak height of substance β, and the concentration of substance β contained in fruits. That is, the controller unit 11 predicts the number of harvestable fruits using the condition data and the chemical data.

The explanatory variables used by the controller unit 11 can be changed as appropriate. For example, when the controller unit 11 predicts the number of harvestable fruits, the number of harvestable fruits before the prediction, the average size, the variation in size, and the like may be incorporated as explanatory variables. That is, when predicting the number of harvestable fruits, the controller unit 11 may predict the number of harvestable fruits by using the status data in addition to the condition data and the chemical data.

Further, when the final data as shown in FIGS. 11A to 11C regarding the cultivation in the previous year are stored, the controller unit 11 may predict the result by performing a multiple regression analysis using the data as well. In this case, the prediction may be made using conditional data and chemical data, or may be made using conditional data, chemical data, and status data. However, with either method, the prediction accuracy can be improved because the amount of data used increases. That is, in the present embodiment, the controller unit 11 can gradually obtain highly reliable prediction results by continuously using the sensing system by the farm worker.

Figure 12:
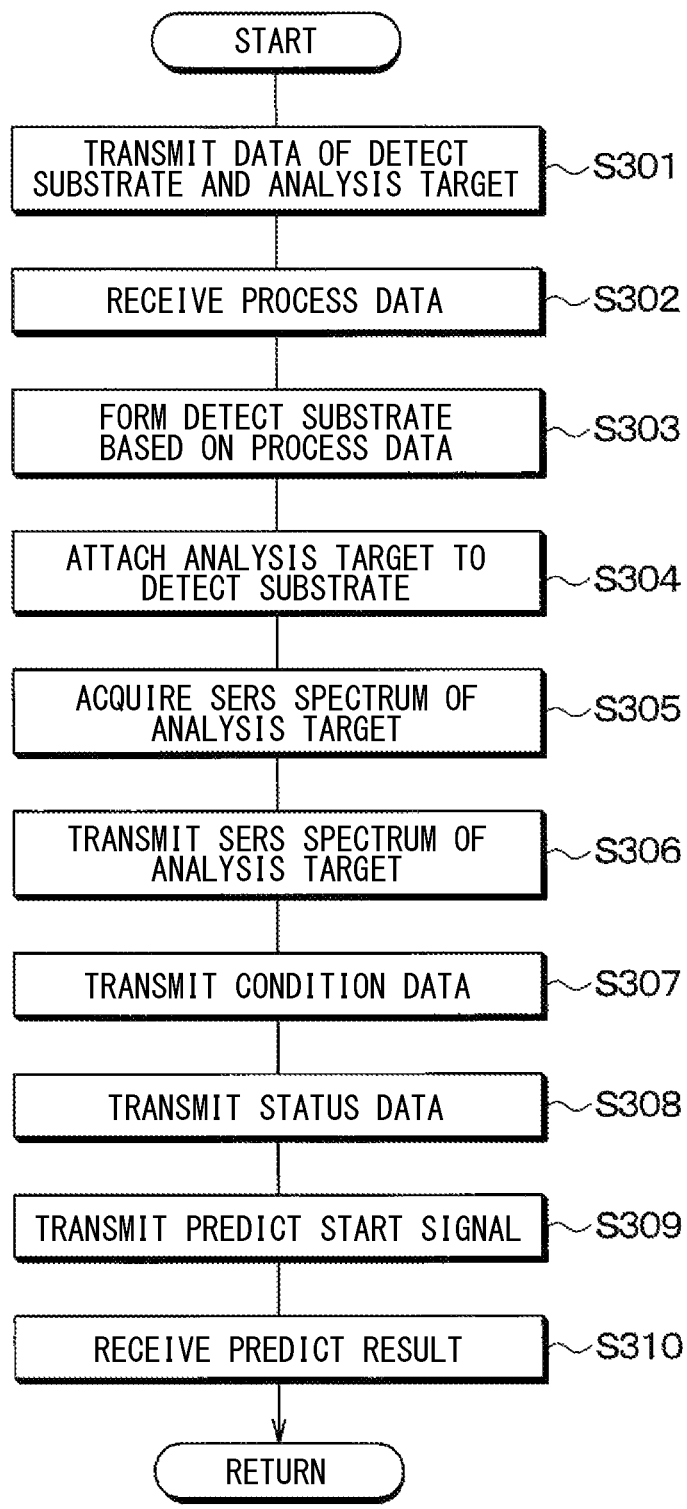
FIG. 12 is a flowchart showing an operation performed by a user according to a second embodiment.

The above has described the configuration of the sensing system in this embodiment. Next, a method of using the sensing system by a farm worker will be described with reference to FIG. 12.

First, the farm worker performs the same steps as in steps S101 to S106 in steps S301 to S306. That is, the farm worker forms the detection substrate 50 based on the processing data, attaches the analysis target 60 to the detection substrate 50, and acquires the SERS spectrum. Then, the farm worker transmits the acquired SERS spectrum from the communication terminal 20 to the server 10. As a result, the server 10 stores chemical data regarding the SERS spectrum.

In the present embodiment, the farm worker attaches the leaf as the analysis target 60 to the detection substrate 50 and acquires the SERS spectrum. Further, after the fruit is produced, the farm worker attaches the leaf and the fruit as the analysis target 60 to the detection substrate 50 and acquires the SERS spectra. In this case, since there are at least two analysis targets 60, at least two concavo-convex structures 50a are formed on the detection substrate 50.

Then, in step S307, the farm worker transmits each condition data from the communication terminal 20 to the server 10. In other words, the farm worker transmits, from the communication terminal 20 to the server 10, the data related to the date and time, the temperature outside the house, the humidity outside the house, the air volume, the amount of solar radiation, the temperature inside the house, the humidity inside the house, the culture solution concentration, the culture solution amount, the number of leaves thinned out, the number of leaves, the average stem thickness, and the stem height. As a result, the server 10 stores data related to the condition data.

Further, in step S308, the farm worker transmits each status data from the communication terminal 20 to the server 10. That is, the farm worker transmits data related to the number of harvestable fruits, the average size, the variation in size, and the number of harvests from the communication terminal 20 to the server 10.number of harvestable fruits, average size, size dispersion, number of harvests As a result, the server 10 stores data related to the status data. When transmitting the SERS spectrum in step S306, the farm worker may concurrently transmit the condition data to be transmitted in step S307 and the status data to be transmitted in step S308.

After that, the farm worker transmits a prediction start signal from the communication terminal 20 to the server 10 in step S309, if necessary. For example, during the growing period, a farm worker transmits a prediction start signal to predict the number of leaves at a later date. Also, for example, during the harvest period, the farm worker transmits a prediction start signal to predict the number of harvestable fruits at a later date. As a result, the server 10 performs multiple regression analysis using various data stored in the storage unit 12. Then, the farm worker receives the prediction result in step S310.

As a result, the farm worker adjusts the parameters that can be adjusted by himself/herself according to the received prediction result. For example, when the predicted number of leaves is smaller than the desired number of leaves during the growing period, the farm worker can carry out measures for promoting growth such as increasing the amount of the culture solution.

Figure 13:
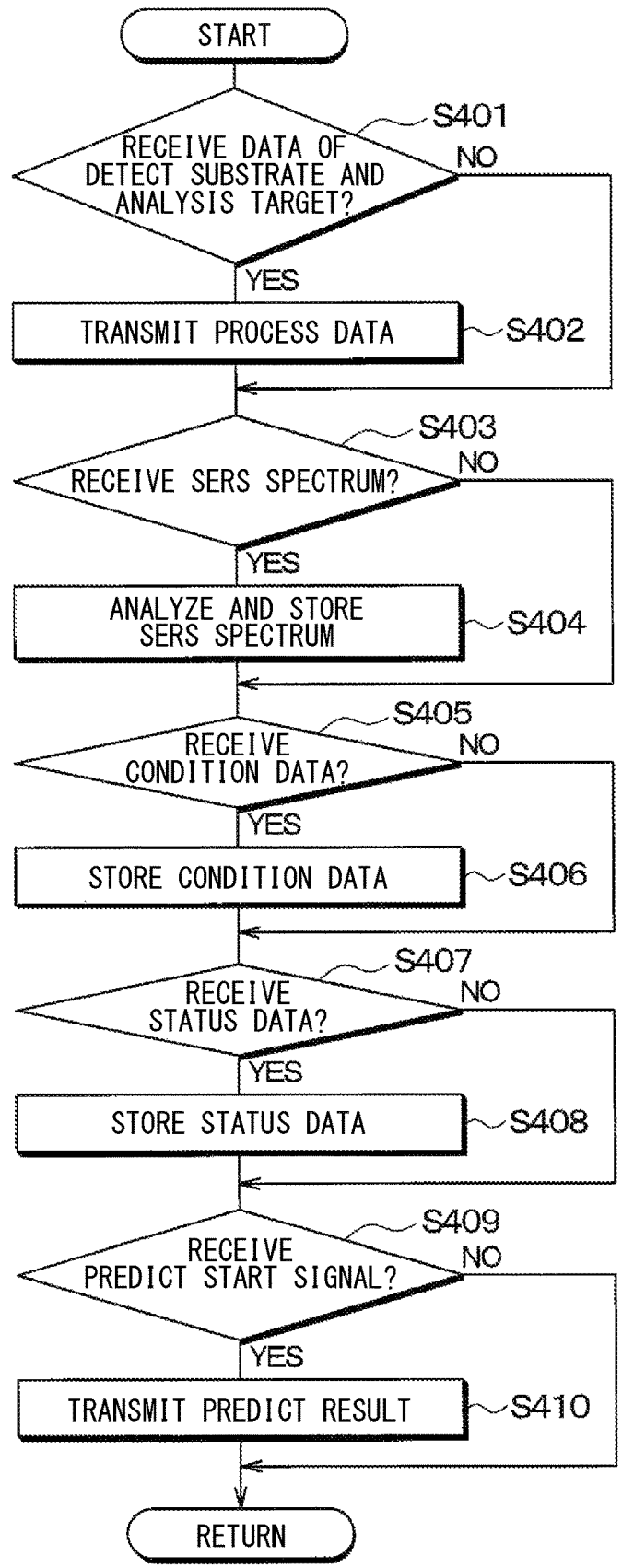
FIG. 13 is a flowchart showing an operation executed by a controller unit of a server according to the second embodiment.

Next, the operation executed by the controller unit 11 in the server 10 in the sensing system will be described with reference to FIG. 13.

First, the controller unit 11 performs the same processing as in steps S201 to S204 in steps S401 to S404. That is, when the controller unit 11 receives the data of the detection substrate 50 and the analysis target 60, the controller unit 11 transmits the processing data. Further, when the controller unit 11 receives the SERS spectrum, the controller unit 11 analyzes the SERS spectrum. In step S404, the controller unit 11 analyzes the SERS spectrum and stores the analysis result as chemical data in the storage unit 12, and also stores the shape of the SERS spectrum itself.

Next, in step S405, the controller unit 11 determines whether or not the condition data is received. Then, when the controller unit 11 determines that the condition data is received (that is, step S405: YES), the controller unit 11 stores the condition data in the storage unit 12 in step S406.

Further, the controller unit 11 determines in step S407 whether or not the status data is received. Then, when the controller unit 11 determines that the status data is received (that is, step S407: YES), the controller unit 11 stores the status data in the storage unit 12 in step S408.

Subsequently, in step S409, the controller unit 11 determines whether or not the prediction start signal is received. Then, when the controller unit 11 determines that the prediction start signal is received (that is, step S409: YES), the controller unit 11 proceeds to step S410. In step S410, the controller unit 11 performs the multiple regression analysis using at least conditional data and chemical data stored in the storage unit 12 to make a prediction, and transmits the prediction result. For example, when the controller unit 11 receives the prediction start signal for predicting the number of leaves at a later date, the controller unit 11 predicts the number of leaves using the condition data and the chemical data stored in the storage unit 12. Further, for example, when the controller unit 11 receives the prediction start signal for predicting the number of harvestable fruits at a later date, the controller unit 11 predicts the number of harvestable fruits using the conditional data and chemical data described in the storage unit 12.

As described above, in the present embodiment, the result after a predetermined period is predicted by using (i) the chemical data related to the SERS spectrum and (ii) the condition data different from the chemical data. Therefore, for example, as compared with the case where the result after a predetermined period is predicted only by the image data, the prediction is performed using the chemical composition of the analysis target 60 while the parameters used for the prediction are increased. Therefore, the accuracy of the prediction result can be improved.

In this embodiment as well, as in the first embodiment, the farm worker may receive chemical data every time the SERS spectrum is transmitted to the server 10, and may always grasp the concentration and the like of the analysis target 60 by himself/herself.

Modified Example of Second Embodiment

A modified example of the second embodiment will be described. In the second embodiment, the controller unit 11 has been described with reference to an example of predicting the yield (that is, the number of harvestable fruits). However, the size of the fruit as a growth amount may be predicted. Further, although not particularly shown, the controller unit 11 may store the number of fruits that have become sick and the rate of sickness, and predict the disease incidence rate.

Then, in the second embodiment, an example of making a prediction about an agricultural product using a sensing system has been described. However, a future outcome of livestock, marine product, or forest product may be predicted. The marine product here means a marine product obtained by aquaculture.

Further, the sensing system of the second embodiment may be applied to predict the probability of occurrence of defective products in a manufacturing process for manufacturing industrial products such as semiconductor devices and in-vehicle parts. For example, suppose that a predetermined industrial product is manufactured by sequentially performing the first step, the second step, the third step, the fourth step, and the fifth step. In this case, for example, when predicting the defective product occurrence probability in the first step, the controller unit 11 may use various data in the first step as explanatory variables and the defective product occurrence probability as an objective variable. Further, for example, when predicting the defective product occurrence probability in the fifth step, the controller unit 11 may use various data of the first to fifth steps as explanatory variables and the defective product occurrence probability as an objective variable. In addition, in various data in each step, for example, temperature, humidity and the like are stored as condition data. In addition, there may be various data in each step. For example, suppose a case where a predetermined gas is generated by a heating step. The detection substrate 50 is exposed to the gas to attach fine particles contained in the gas to the detection substrate 50 to acquire the SERS spectrum. The data related to the SERS spectrum is stored as chemical data. Then, the probability of defective product occurrence in each step is stored as status data. In this case, the status data may be the life of the product manufactured as a non-defective product.

Further, the sensing system of the second embodiment may be applied to predict the cleanliness in a predetermined space such as a vehicle interior space. For example, it can be applied to predict the cleanliness of the interior space of a car-sharing vehicle. That is, in such a case, for example, the vehicle interior temperature, the vehicle interior humidity, the air conditioner temperature, the air conditioner air volume, the number of occupants, and the vehicle interior image are stored as condition data. Further, by attaching fine particles or the like existing in the space inside the vehicle to the detection substrate 50 and acquiring the SERS spectrum, the data related to the SERS spectrum is stored as chemical data. Then, the controller unit 11 may predict the cleanliness after a lapse of a predetermined period by using these condition data and the chemical data as explanatory variables and the cleanliness in the vehicle as an objective variable. However, in such a case, it is preferable to mount the measuring apparatus 40 in the vehicle interior. Then, it is preferable to form the detection substrate 50 on which the concavo-convex structure 50a corresponding to the fine particles that are assumed to exist in the vehicle is formed in advance so that the cleanliness after a predetermined period can be immediately predicted in the vehicle interior. In this case, for example, the person who boarded earlier predicts the cleanliness, and the person who rides later confirms the predicted cleanliness to determine the time to board. By doing so, it is possible to provide a comfortable environment for each occupant.

Third Embodiment

In the present embodiment, the controller unit 11 in the server 10 predicts an adjustment method so as to be the desired status of the farm worker, as compared with the second embodiment. Others are the same as those in the second embodiment, and thus the description thereof will be omitted here.

Various data similar to those of the second embodiment are stored in the storage unit 12 of the present embodiment. Then, when the controller unit 11 receives an adjustment start signal from the farm worker, the controller unit 11 uses the above Expression 1 to predict a parameter adjustment method that the farm worker can adjust so as to approach the desired status desired by the farm worker. Specifically, the controller unit 11 predicts a method of adjusting condition data that can be adjusted by the farm worker.

For example, suppose a case where the farm worker receives the expected result regarding the average size at a later date in step S310. In such a case, if the received expected result is different from the average size that the farm worker wants, the farm worker may want to know in detail how to adjust to the average size that the farm worker wants.

In this case, when the controller unit 11 receives the adjustment start signal regarding the average size, the controller unit 11 predicts the adjustment method for approaching the desired status by using the various data. For example, the controller unit 11 calculates the partial regression coefficient β (ti) as shown in FIG. 14 by storing various data similar to those in the second embodiment in the storage unit 12. Note that FIG. 14 is a simplified diagram of the data stored in the storage unit 12, and may include status data.

Then, for example, the farm worker wants to know the adjustment method for increasing the average size when the acquired expected result of the average size is smaller than the desired average size. In this case, the simplest adjustment method for the farm worker is to increase the value of the explanatory variable X (ti) having the largest partial regression coefficient β (ti). Therefore, the controller unit 11 extracts the explanatory variable X (ti) having the largest partial regression coefficient β (ti) from the condition data that can be controlled by the farm worker. The controller unit 11 then calculates the value of the explanatory variable X (ti) for approaching the average size desired by the farm worker. For example, in the case of the data shown in FIG. 14, since the partial regression coefficient β (ti) has the largest value of 2, the controller unit 11 predicts a method for adjusting the amount of the culture solution as the explanatory variable X (ti) and transmits the adjustment result.

Further, for example, when the acquired expected result of the average size is larger than the desired average size, the farm worker wants to grasp the adjustment method for reducing the average size. In this case, the simplest adjustment method for the farm worker is to reduce the value of the explanatory variable X (ti) having the smallest partial regression coefficient β (ti). Therefore, the controller unit 11 extracts the explanatory variable X (ti) having the smallest partial regression coefficient β (ti) from the condition data that can be controlled by the farm worker. The controller unit 11 then calculates the value of the explanatory variable X (ti) for approaching the average size desired by the farm worker. For example, in the case of the data shown in FIG. 14, the partial regression coefficient β (ti) has the smallest value of −0.8, so that the controller unit 11 adjusts the number of leafs thinned out as the explanatory variable X (ti) and transmits the adjustment result.

Figure 15:
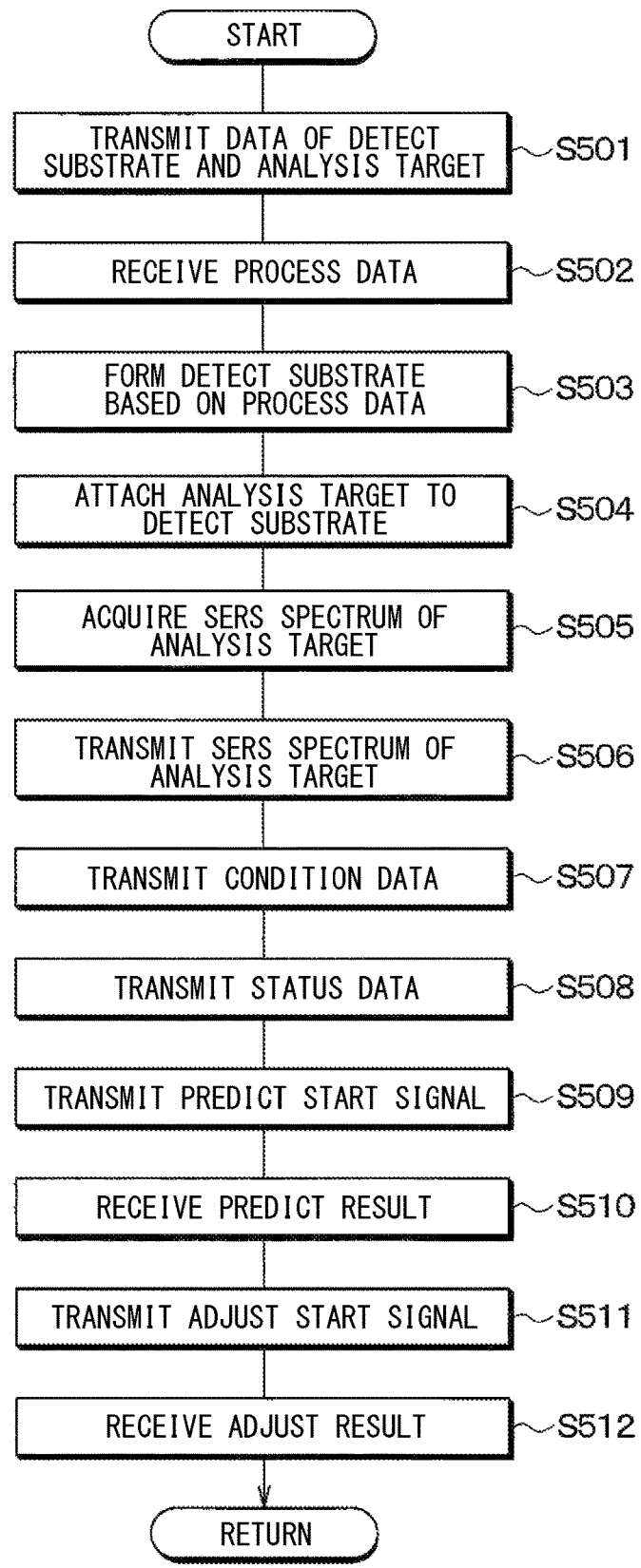
FIG. 15 is a flowchart showing an operation performed by a user according to the third embodiment.

The above has described the configuration of the sensing system in this embodiment. Next, a method of using the sensing system by a farm worker will be described with reference to FIG. 15.

First, the farm worker performs the same steps as in steps S301 to S310 in steps S501 to S510. Then, the farm worker transmits an adjustment start signal from the communication terminal 20 to the server 10 in step S511, if necessary. For example, a farm worker transmits an adjustment start signal that predicts the adjustment needed to achieve the desired size at a later date. As a result, the server 10 predicts the method of adjusting the parameters that can be controlled by the farm worker in the condition data stored in the storage unit 12 as described above. Then, the farm worker receives the adjustment result in step S512. As a result, the farm worker can clearly grasp the detailed adjustment method for achieving the desired status, and can carry out cultivation to approach the desired status.

Figure 16:
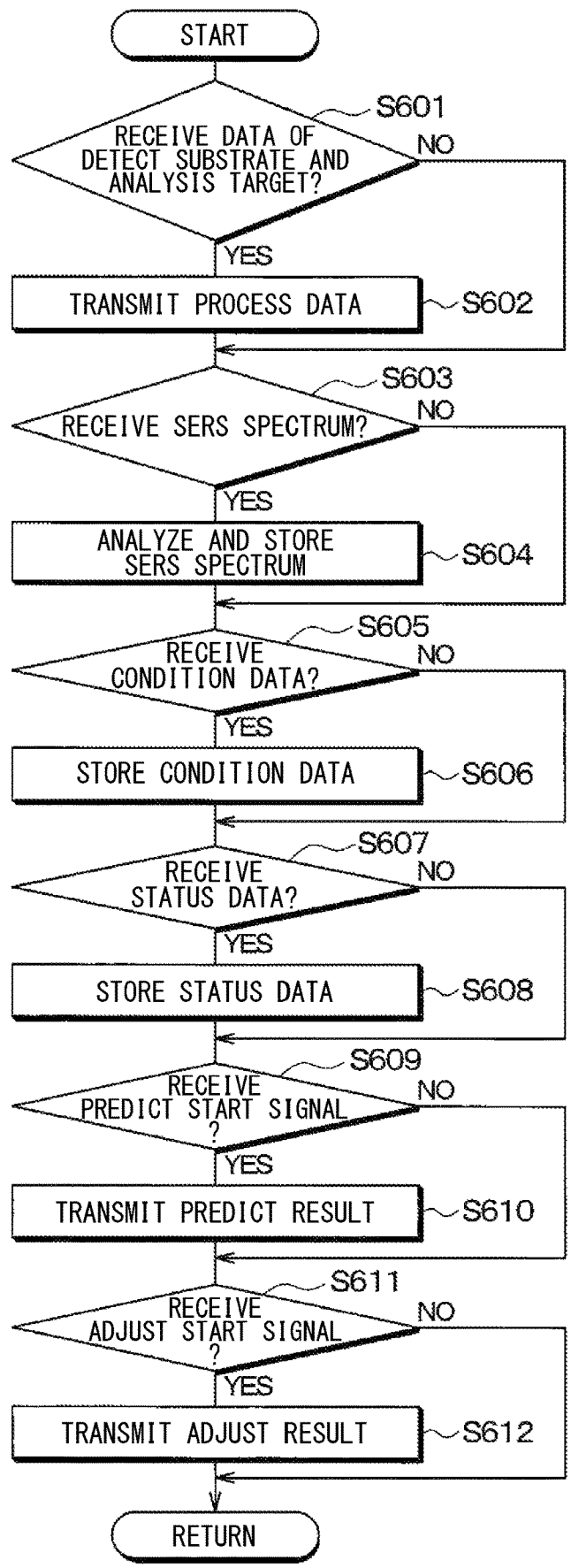
FIG. 16 is a flowchart showing an operation executed by a controller unit in a server according to the third embodiment.

Next, the operation executed by the controller unit 11 in the server 10 in the sensing system will be described with reference to FIG. 16.

First, the controller unit 11 performs the same processing as in steps S401 to S410 in steps S601 to S610. Then, in step S611, the controller unit 11 determines whether or not the adjustment start signal is received. Then, when the controller unit 11 determines that the adjustment start signal is received (that is, step S611: YES), the controller unit 11 proceeds to step S612. In step S612, the controller unit 11 predicts the method of adjusting the parameters that can be controlled by the farm worker in the condition data stored in the storage unit 12 as described above. Then, the controller unit 11 transmits the predicted adjustment result. For example, the controller unit 11 predicts the adjustment method required to make the average size the size desired by the farm worker, and transmits the predicted adjustment result.

As described above, in the present embodiment, a method of adjusting parameters that can be controlled by the farm worker in the condition data is predicted. Therefore, the farm worker can perform a process for approaching the desired status based on the predicted adjustment result.

Further, when predicting the adjustment method, the controller unit 11 extracts an explanatory variable X (ti) to be adjusted according to the value of the partial regression coefficient β (ti). Then, the partial regression coefficient β (ti) is calculated using at least conditional data and chemical data as described in the second embodiment. Therefore, for example, as compared with the case where the adjustment method is predicted only from the image data, the prediction is performed using the chemical composition of the analysis target 60, and the parameters used for the prediction are increased. Therefore, the accuracy of the prediction result can be improved.

Modified Example of Third Embodiment

A modified example of the third embodiment will be described. The sensing system of the third embodiment can be applied to a livestock product, a marine product, or a forest product as well as the modified examples of the second embodiment. Further, the sensing system of the third embodiment can be applied to a manufacturing process related to an industrial product, and can also be applied to a cleanliness in a predetermined space.

Other Embodiments

Although the present disclosure has been described in accordance with embodiments, it is understood that the present disclosure is not limited to such embodiments or structures. The present disclosure also includes various modifications and modifications within an equal range. In addition, various combinations and forms, as well as other combinations and forms including only one element, more than that, or less than that, are also within the scope and idea of the present disclosure.

For example, each of the above embodiments has described the example in which the server 10 is provided with the controller unit 11 having the storage unit 12. However, a processing unit such as a CPU that performs a predetermined process and a storage unit 12 may be separately provided. Further, although processing data, analysis data, and the like are stored in the storage unit 12, each data may be provided in a plurality of storage units instead of one storage unit. In this case, a plurality of servers 10 may be provided.

Further, in each of the above embodiments, the processing apparatus 30 and the measuring apparatus 40 may be integrated. According to this, since the laser irradiation units used in the processing apparatus 30 and the measuring apparatus 40 can be integrated, the system can be simplified. That is, since at least a part of the processing unit 31 and the measuring unit 41 can be integrated, the system can be simplified.

Further, in each of the above embodiments, the processing apparatus 30 and the server 10 may be electrically connected, or the measuring apparatus 40 and the server 10 may be electrically connected.

Further, in each of the above embodiments, the measuring apparatus 40 may detect the infrared spectroscopic spectrum by infrared spectroscopic analysis. In such a case, the storage unit 12 stores the processing data and the analysis data related to the infrared spectroscopic spectrum, and the controller unit 11 analyzes the infrared spectroscopic spectrum using the analysis data.

Further, in each of the above embodiments, as the communication terminal 20, a terminal for communicating between the server 10 and the processing apparatus 30 and another terminal for communicating between the server 10 and the measuring apparatus 40 may be separately provided. In this case, each communication terminal 20 may be provided integrally with the processing apparatus 30 or the measuring apparatus 40.

Further, in each of the above embodiments, (i) the processing data transmitted from the server 10 to the communication terminal 20 and (ii) the SERS spectrum transmitted from the measuring apparatus 40 to the communication terminal 20 and transmitted from the communication terminal 20 to the server 10 may be encrypted by an encryption method. According to this, it is possible to prevent the user from illegally using each data.

Further, in each of the above embodiments, the method for forming or building the detection substrate 50 having the concavo-convex structure 50a can be appropriately changed, and may be as follows. For example, first, a metal substrate made of gold, silver, or the like is prepared separately from the detection substrate 50. Then, the metal substrate may be irradiated with a laser beam to disperse the metal particles, and the scattered metal particles may be deposited on the detection substrate 50 to form the detection substrate 50 having the concavo-convex structure 50a. In this case, the detection substrate 50 prepared first may be glass, a rubber sheet, or the like. Further, the detection substrate 50 having the concavo-convex structure 50a may be formed by performing the blast treatment.

The controller (i.e., the controller unit 11, the controller 33, the controller 43) and methods described in the present disclosure in the above embodiments may be implemented by one or more special-purpose computers. Such computers may be created (i) by configuring (a) a memory and a processor programmed to execute one or more particular functions embodied in computer programs, or (ii) by configuring (b) a processor provided by one or more special purpose hardware logic circuits, or (iii) by configuring a combination of (a) a memory and a processor programmed to execute one or more particular functions embodied in computer programs and (b) a processor provided by one or more special purpose hardware logic circuits. The computer programs may be stored, as instructions to be executed by a computer, in a tangible non-transitory computer-readable storage medium.

For reference to further explain features of the present disclosure, the description is added as follows.

There is proposed a method of identifying a substance or the like as an analysis target with a surface-enhanced Raman Spectroscopy (hereinafter, simply referred to as SERS) method. Specifically, in this method, first, a concavo-convex structure is formed on the surface of the detection substrate, and the analysis target is attached to the portion where the concavo-convex structure is formed. Then, by irradiating the analysis target with a laser beam in this state, the SERS spectrum corresponding to the analysis target is acquired.

There is a demand that consumers and producers want to easily investigate substances and the like contained in an analysis target such as an agricultural product. It is thus desired to provide (i) a sensing system capable of easily investigating an analysis target and (ii) a data structure used in the sensing system.

Aspects of the present disclosure described herein are set forth in the following clauses.

According to an aspect of the present disclosure, a data structure is provided to be stored in a non-transitory storage medium in a server capable of communicating with a communication terminal used by a user. The data structure includes a processing data and an analysis data. The processing data is relating to a processing condition to form a concavo-convex structure on a detection substrate, the processing data being used to perform a spectroscopic analysis to an analysis target attached to the concavo-convex structure formed on the detection substrate. The analysis data is to analyze the analysis target from a spectral spectrum of the analysis target obtained by performing the spectroscopic analysis. Herein, the processing data and the analysis data are set for each of a plurality of the analysis targets.

According to this, the user can easily acquire the processing data and form the detection substrate by communicating with the server. The analysis target can be easily analyzed by transmitting the spectroscopic spectrum. Therefore, the analysis target can be easily investigated.

According to another aspect of the present disclosure, a sensing system is provided to include: a server including (i) a storage configured to store a predetermined data and (ii) a controller configured to perform a predetermined process using data stored in the storage; and a communication terminal used by a user, the communication terminal being configured to communicate with the server. Herein, the storage is further configured to store (i) a processing data relating to a processing condition to form a concavo-convex structure on a detection substrate, the processing data being used to perform a spectroscopic analysis to an analysis target attached to the concavo-convex structure formed on the detection substrate, and (ii) an analysis data to analyze the analysis target from a spectroscopic spectrum of the analysis target obtained by performing the spectroscopic analysis. The processing data and the analysis data are set for each of a plurality of the analysis targets. The controller in the server is further configured to receive a signal from the communication terminal for requesting the processing data relating to the detection substrate used to analyze the analysis target, select the processing data corresponding to (i) the analysis target and (ii) a material included in the detection substrate, and transmit the selected processing data to the communication terminal. The communication terminal is further configured to receive the processing data that is used to form the detection substrate on which the concavo-convex structure is formed while the analysis target is attached to the concavo-convex structure, to obtain the spectroscopic spectrum by the spectroscopic analysis. The communication terminal is further configured to transmit the spectroscopic spectrum obtained by the spectroscopic analysis. The controller in the server is further configured to analyze the spectroscopic spectrum using the analysis data in response to receiving the spectroscopic spectrum from the communication terminal.

According to this, when receiving the signal requesting the processing data, the controller is configured to transmit the processing data; when receiving the spectroscopic spectrum, the controller is configured to analyze the spectroscopic spectrum. Therefore, the user can easily acquire the processing data for forming the detection substrate having the concavo-convex structure suitable for the analysis target from the server. In addition, the user can easily analyze the analysis target by transmitting the spectroscopic spectrum to the server. Therefore, the user can easily investigate the analysis target.

What is claimed is:

1. A data structure stored in a non-transitory storage medium in a server capable of communicating with a communication terminal used by a user,
the data structure comprising:
a processing data relating to a processing condition to form a concavo-convex structure on a detection substrate, the processing data being used to perform a spectroscopic analysis to an analysis target attached to the concavo-convex structure formed on the detection substrate; and
an analysis data to analyze the analysis target from a spectral spectrum of the analysis target obtained by performing the spectroscopic analysis,
wherein:
the processing data and the analysis data are set for each of a plurality of the analysis targets,
further comprising:
a chemical data based on the spectroscopic spectrum that is obtained and transmitted by the user; and
a conditional data temporally relating to the chemical data, the condition data being based on a condition relating to the analytical target, the condition data being obtained in a manner different from the spectroscopic spectrum and transmitted by the user,
wherein:
the chemical data and the condition data are associated with each other.

2. The data structure according to claim 1, further comprising:
a status data temporally relating to the chemical data, the status data being based on a status of the analysis target, the status data being obtained in a manner different from the spectroscopic spectrum and transmitted by the user,
wherein:
the chemical data, the condition data, and the status data are associated with each other.

3. The data structure according to claim 2, wherein:
the status data is (i) a growth amount, a yield, or a disease incidence of an agriculture, forestry, and fishery product, (ii) a life of an industrial product, (iii) a probability of a defective product in a manufacturing process, or (iv) a cleanliness within a predetermined space.

4. The data structure according to claim 1, wherein:
the processing data relates to a concavo-convex structure when surface-enhanced Raman spectroscopy is performed.

5. A sensing system comprising:
a server including (i) a storage configured to store a predetermined data and (ii) a controller configured to perform a predetermined process using data stored in the storage; and
a communication terminal used by a user, the communication terminal being configured to communicate with the server,
wherein:
the storage is further configured to store
(i) a processing data relating to a processing condition to form a concavo-convex structure on a detection substrate, the processing data being used to perform a spectroscopic analysis to an analysis target attached to the concavo-convex structure formed on the detection substrate, and
(ii) an analysis data to analyze the analysis target from a spectroscopic spectrum of the analysis target obtained by performing the spectroscopic analysis;
the processing data and the analysis data are set for each of a plurality of the analysis targets;
the controller is further configured to
receive, from the communication terminal, a signal requesting the processing data relating to the detection substrate used to analyze the analysis target,
select the processing data corresponding to (i) the analysis target and (ii) a material included in the detection substrate, and
transmit the selected processing data to the communication terminal;
the communication terminal is further configured to
receive the processing data that is used to form the detection substrate on which the concavo-convex structure is formed while the analysis target is attached to the concavo-convex structure, to obtain the spectroscopic spectrum by the spectroscopic analysis, and
transmit the spectroscopic spectrum obtained by the spectroscopic analysis; and
the controller is further configured to analyze the spectroscopic spectrum using the analysis data in response to receiving the spectroscopic spectrum from the communication terminal.

6. The sensing system according to claim 5, wherein:
the controller is further configured to
store a chemical data based on the spectroscopic spectrum in the storage each time the spectroscopic spectrum is received, and
store a condition data in the storage each time the condition data is received, the condition data being relating to the analysis target, the condition data being temporally related to the chemical data, the condition data being obtained in a manner different from the spectroscopic spectrum;
the chemical data and the condition data are stored in the storage in association with each other; and
the controller is further configured to predict a status of the analysis target after a predetermined period of time based on the chemical data and the condition data stored in the storage in response to receiving a prediction start signal from the communication terminal.

7. The sensing system according to claim 6, wherein:
the controller is further configured to store a status data each time the status data is received, the status data being temporally relating to the chemical data, the status data being based on the status of the analysis target, the status data being obtained in a manner different from the spectroscopic spectrum and transmitted by the user;
the chemical data, the condition data, and the status data are stored in the storage in association with each other; and
the controller is further configured to predict the status of the analysis target after a predetermined period of time based on the chemical data, the condition data, and the status data stored in the storage, in response to receiving a prediction start signal from the communication terminal.

8. The sensing system according to claim 6, wherein:
the condition data includes a data enabled to be controlled by the user; and
in response to receiving an adjustment start signal for setting the status of the analysis target as a desired status from the communication terminal, the controller is further configured to predict an adjustment method of the data enabled to be controlled by the user to bring the status of the analysis target after a predetermined period of time closer to the desired status.

9. The sensing system according to claim 6, wherein:
the controller is further configured to predict, as the status of the analysis target after the predetermined period of time, (i) a growth amount, a yield, or a disease incidence of an agriculture, forestry, and fishery product, (ii) a life of an industrial product, (iii) a probability of a defective product in a manufacturing process, or (iv) a cleanliness within a predetermined space.

10. The sensing system according to claim 5, further comprising:
a processing apparatus configured to be communicable with the communication terminal, the processing apparatus forming the concavo-convex structure on the detection substrate based on the processing data in response to receiving the processing data from the communication terminal; and
a measuring apparatus configured to be communicable with the communication terminal, the measuring apparatus acquiring the spectroscopic spectrum of the analysis target by the spectroscopic analysis and transmitting the acquired spectroscopic spectrum to the communication terminal, in response to the detection substrate being arranged, the detection substrate in which the analysis target is attached to the concavo-convex structure.

11. The sensing system according to claim 10, wherein:
the processing apparatus is further configured to form the concavo-convex structure on the detection substrate by irradiating the detection substrate with a laser beam.

12. The sensing system according to claim 11, wherein:
the processing apparatus and the measuring apparatus are integrated into each other; and
the measuring apparatus is further configured to radiate the laser beam to perform the spectroscopic analysis.

13. The sensing system according to claim 10, wherein:
the server is capable of transmitting and receiving data to and from the processing apparatus and the measuring apparatus via the communication terminal.

14. A non-transitory storage medium storing a data structure to a server communicably connected to a communication terminal used by a user,
the data structure comprising:
a processing data relating to a processing condition to form a concavo-convex structure on a detection substrate, the processing data being used to perform a spectroscopic analysis to an analysis target attached to the concavo-convex structure formed on the detection substrate; and
an analysis data to analyze the analysis target from a spectral spectrum of the analysis target obtained by performing the spectroscopic analysis,
wherein:
the processing data and the analysis data are set for each of a plurality of the analysis targets,
the data structure further comprises:
a chemical data based on the spectroscopic spectrum obtained and transmitted by the user; and
a conditional data temporally relating to the chemical data, the condition data being based on a condition relating to the analytical target, the condition data being obtained in a manner different from the spectroscopic spectrum and transmitted by the user,
wherein the chemical data and the condition data are associated with each other.

15. The non-transitory storage medium according to claim 14, wherein
the data structure further comprises:
a status data temporally relating to the chemical data, the status data being based on a status of the analysis target, the status data being obtained in a manner different from the spectroscopic spectrum and transmitted by the user,
wherein:
the chemical data, the condition data, and the status data are associated with each other.

16. The non-transitory storage medium according to claim 15, wherein:
the status data is a growth amount, a yield, or a disease incidence of an agriculture, forestry, and fishery product, a life of an industrial product, a probability of a defective product in a manufacturing process, or a cleanliness within a predetermined space.

17. The non-transitory storage medium according to claim 14, wherein:
the processing data relates to a concavo-convex structure when surface-enhanced Raman spectroscopy is performed.

* * * * *